United States Patent [19]
Cantrall et al.

[11] Patent Number: 5,530,551
[45] Date of Patent: Jun. 25, 1996

[54] METHOD FOR APPARATUS FOR DETERMINING MEASUREMENT PARAMETER OF A FIBROUS OBJECT AND WHETHER THE OBJECT IS A VALID OBJECT

[75] Inventors: Chistopher J. Cantrall, Normanhurst; Timothy P. Dabbs, West Ryde; Monty Glass, Dulwich Hill; William Humphries, Narara; Leslie J. Wills, Berala, all of Australia

[73] Assignee: Commonwealth Scientific and Industrial Research, Australia

[21] Appl. No.: 199,298

[22] PCT Filed: Sep. 2, 1992

[86] PCT No.: PCT/AU92/00465

§ 371 Date: Mar. 2, 1994

§ 102(e) Date: Mar. 2, 1994

[87] PCT Pub. No.: WO93/05359

PCT Pub. Date: Mar. 18, 1993

[30] Foreign Application Priority Data

Sep. 6, 1991 [AU] Australia ................... PK8251

[51] Int. Cl.⁶ .................................................. G01B 11/00
[52] U.S. Cl. .................. 356/394; 356/384; 356/335; 356/357
[58] Field of Search .................... 356/394, 384, 356/385, 386, 238, 345, 351, 354, 355, 357, 335–343

[56] References Cited

U.S. PATENT DOCUMENTS

| | | | |
|---|---|---|---|
| 3,518,007 | 6/1970 | Ito | 356/357 |
| 3,643,101 | 2/1972 | Shipp et al. | 356/384 |
| 3,680,961 | 8/1972 | Rudd | 356/335 |
| 3,719,425 | 3/1973 | Leitz et al. | 356/384 |
| 3,851,169 | 11/1974 | Faxvog | 250/222 |
| 4,046,536 | 9/1977 | Smithgall, Sr. | 356/385 |
| 4,053,229 | 10/1977 | McCluney | 356/339 |
| 4,266,874 | 5/1981 | Tanin et al. | 356/335 |
| 4,623,252 | 11/1986 | Hollenbeck | 356/338 |
| 4,650,322 | 3/1987 | Fejer et al. | 356/385 |
| 4,837,446 | 6/1989 | Renard et al. | 250/461.1 |
| 5,161,053 | 11/1992 | Dabbs | 359/384 |

FOREIGN PATENT DOCUMENTS

| | | |
|---|---|---|
| 5786873 | 1/1975 | Australia . |
| 5148579 | 4/1980 | Australia . |
| 7484391 | 9/1991 | Australia . |
| 0225009 | 6/1987 | European Pat. Off. . |
| 351436 | 1/1990 | European Pat. Off. . |
| 657554 | 9/1986 | Switzerland . |
| 1067457 | 5/1967 | United Kingdom . |
| 1116009 | 6/1968 | United Kingdom . |

OTHER PUBLICATIONS

Patent Abstracts of Japan, vol. 16, No. 203, 14 May 1992, JP-A-04 030 916.
Supplementary European Search Report EP 92 91 9271.
International Search Report to Application No. PCT/AU92/00465.
International Preliminary Examination Report to Application No. PCT/AU92/00465.

*Primary Examiner*—Hoa Q. Pham
*Attorney, Agent, or Firm*—Dressler, Goldsmith Shore & Milnamow, Ltd.

[57] ABSTRACT

Disclosed is a method/apparatus to determine any one of a plurality of parameters: shape, area, chemical composition, diameter, color, number, thickness, width, length, absorptivity, reflectivity, transmittivity, dielectric constant, raman scattering profile, fluorescence, surface tension, roughness, profile, density, position and orientation. Also use of a plurality of energy beams as source energy: charged and neutral particle beams, gamma-, X-, micro-, optical and acoustic waves. The described apparatus determines the mean and standard deviation of a plurality of diameters of wool fibers, and includes a He-Ne laser (101), and a pinhole (102) which produce an expanding laser beam which passes through cell (105). Beam splitter (103) is operatively disposed to pinhole (102) and laser (101) to direct a portion of the laser beam to reference detector (109) which is electrically connected to processor (110) via line (111). When (Abstract continued on next page.)

apparatus (100) is operating wool fibers in an isopropanol-wool slurry pass through cell (105) generally at a non-zero degree angle to the direction of slurry flow through cell (105) to interact with the laser beam in cell (105). Beam splitter (104) and microscope objective (106) are operatively disposed with respect to laser (101), pinhole (102) and cell (105) to produce an in focus magnified transmission image of wool fibers in cell (105) in the plane of end (107) of optical fiber bundle (108). Each of the fibers in bundle (108) is connected to a photodiode detector (112). Processor/timer (113) is connected electrically to detector (112) by line (114). Processor/timer (113) is also connected electrically to computer (115) by line (116) and to processor (110) by line (117). Detector (118) is connected electrically to processor (110) by line (119). Processor (110) is connected electrically to computer (115) by line (120). Detector (118) is operatively disposed with respect to laser (101), pinhole (102) and cell (105) to detect outgoing light.

33 Claims, 8 Drawing Sheets

METHOD FOR APPARATUS FOR DETERMINING MEASUREMENT PARAMETER OF A FIBROUS OBJECT AND WHETHER THE OBJECT IS A VALID OBJECT

This invention relates to methods and apparatus for determining a measurement parameter(s) of an object and whether the object is a valid object, for determining a first parameter(s) of a valid object, for determining a measurement parameter(s) of a valid object, for determining a measurement parameter(s) of an invalid object, for determining a first parameter(s) of an object and determining a first parameter(s) of an invalid object, for determining a measurement parameter(s) of a valid object and determining a measurement parameter(s) of an invalid object, for determining a measurement parameter(s) of a valid object and determining a first parameter(s) of a valid object, for determining a measurement parameter(s) and a first parameter(s) of a valid object and determining a measurement parameter(s) of an invalid object, for determining a measurement parameter(s) of a valid object and determining a first parameter(s) of an invalid object, for determining a first parameter(s) of a valid object and determining a measurement parameter(s) of an invalid object, and for determining a first parameter(s) of a valid object and determining a first parameter(s) of an invalid object.

BACKGROUND ART

A number of methods and apparatus have been developed for obtaining a measurement of mean fibre diameter and fibre diameter distribution in a sample containing; a plurality of wool fibres having different diameters.

Two classes of instruments for the measurement of mean fibre diameter are:

1. Those which give an estimate of average diameter only.
2. Those which also give the distribution of fibre diameters within a sample including statistical information such as the variance of the diameters of the sample fibres.

In recent times the information given by the distribution of wool fibre diameter has come to be accepted as being required in some circumstances.

To accurately estimate the distribution of the fibre diameters a large number of measurements have to be made.

A particular method for measuring mean fibre diameter and fibre diameter distribution involves the measurements of fibre diameters in an optical microscope using a calibrated graticule to gauge the fibre diameters. This method is slow, tedious and prone to errors. These errors can arise from a number of sources including the optics, the conditioning of the fibres, and the judgment of the operators. Measurement of a few thousand fibres using this technique takes many hours to complete.

An instrument for determining fibre diameter distribution has been proposed by Lynch and Michie, Australian Patent No. 472,862 entitled "Optical Shadowing Method and Apparatus for Fibre Diameter Measurement".

In the apparatus described in 472,862 a light beam traverses a transparent measurement cell and falls on a photoelectric sensor.

Fibres dispersed and suspended in a clear liquid are caused to flow through the measurement cell and intercept the light beam. The reduction in the detected light intensity as a result of a fibre properly occluding the light beam is a function of the diameter of the fibre.

The apparatus includes a split photodetector and a processor to reject readings when a fibre end falls within the light beam. Ensuring that the amplitude of the signal from the two detecting elements of the split photodetector differed by less than 10%, was thought to be sufficient for acceptance of the measurement.

Instruments manufactured according to the teaching of the Lynch and Michie patent have been available for many years and are used to measure the diameter distribution of wool and other fibres.

Over this period a number of deficiencies, some of which are related to the validity of the individual fibre measurements, have become apparent.

Firstly, equal light occlusion on the two halves of the split detector is not sufficient to guarantee the validity or otherwise of a measurement. For example it has been observed that the diameter of some fibres varies more than 30% in less length than the beam diameter. These fibres can give an unequal response from the two halves of the split detector circuitry which would in turn reject the measurement, even though the measurement should have been accepted. Alternatively, measurements of fibres that have not fully crossed the light beam have been observed to have been accepted when they should have been rejected.

Secondly, the Lynch and Michie proposal assumed that the fibre snippets would be so dilute in the carrier liquid that the probability of two fibres being in the light beam at the same time would be negligible.

In practice, it has been found that for a typical measurement rate of 100 fibres per second the proportion of occurrence where two fibres appear in the light beam at the same time is significant. This effect appears in the diameter distribution graph as a second hump at double the value of the real distribution hump. The second hump has a significant affect on the second moment statistic, the variance.

The Lynch and Michie patent did not teach a method for rejecting the signals representing the occurrence of two fibres measured simultaneously in the light beam, but practical realisation of the instrument has included an apparatus whereby signal responses with a double peak were interpreted as representing two fibres in the beam simultaneously and were therefore rejected.

Observations have shown that the double peak detector does not pick up all multiple fibre events.

OBJECTS OF INVENTION

Objects of this invention are to provide methods and apparatus for determining a measurement parameter(s) of an object and whether the object is a valid object, for determining a first parameter(s) of a valid object, for determining a measurement parameter(s) of a valid object, for determining a measurement parameter(s) of an invalid object, for determining a first parameter(s) of an object and determining a first parameter(s) of an invalid object, for determining a measurement parameter(s) of a valid object and determining a measurement parameter(s) of an invalid object, for determining a measurement parameter(s) of a valid object and determining a first parameter(s) of a valid object, for determining a measurement parameter(s) and a first parameter(s) of a valid object and determining a measurement parameter(s) of an invalid object, for determining a measurement parameter(s) of a valid object and determining a first parameter(s) of an invalid object, for determining a first parameter(s) of a valid object and determining a measurement parameter(s) of an invalid object, and for determining a first parameter(s) of a valid object and determining a first parameter(s) of an invalid object.

DISCLOSURE OF THE INVENTION

According to a first embodiment of this invention there is provided a method for determining a measurement parameter(s) of an object and whether the object is a valid object, comprising:

(a) passing a validating energy beam(s) through a validating interaction volume(s);

(b) detecting validating outgoing energy originating from the validating energy beam(s) in the validating interaction volume(s), the detection being in at least one validating focal plane of the validating outgoing energy with respect to the validating interaction volume(s) and determining a validating parameter(s) from the detected validating outgoing energy;

(c) determining from the validating parameter(s) whether the validating outgoing energy originated from an interaction between an object and the validating beam(s) in the validating volume(s) and, on determining an object;

(d) locating the object in a measurement interaction volume(s);

(e) passing a measurement energy beam(s) through the measurement interaction volume(s) to interact with the object so as to produce measurement outgoing energy;

(f) detecting at least a portion of the measurement outgoing energy in at least one measurement focal plane of the measurement outgoing energy with respect to the measurement interaction volume(s), the measurement focal plane being different from the validating focal plane, and determining a measurement parameter(s) from the detected measurement outgoing energy; and (g) determining from the validating parameter(s) whether the object is a valid object.

According to a second embodiment of this invention there is provided a method for determining a first parameter(s) of a valid object, comprising:

the method of the first embodiment; and, on determining a valid object, (i') determining the first parameter(s) of the valid object from the measurement parameter(s); and (j') determining the first parameter(s) of the valid object as an acceptable valid object parameter(s).

According to a third embodiment of this invention there is provided a method for determining a measurement parameter(s) of a valid object, comprising:

the method of the first embodiment; and, on determining a valid object, (h') determining the measurement parameter(s) of the valid object as an acceptable valid object parameter(s).

According to a fourth embodiment of this invention there is provided a method for determining a measurement parameter(s) of an invalid object, comprising:

the method of the first embodiment; and, on determining an invalid object, (h") determining the measurement parameter(s) of the invalid object as an unacceptable valid object parameter(s).

According to a fifth embodiment of this invention there is provided a method for determining a first parameter(s) of an object and determining a first parameter(s) of an invalid object, comprising:

steps (a) to (g) of the first embodiment;

(i) determining the first parameter(s) of the object from the measurement parameter(s); and, on determining an invalid object, (j''') determining the first parameter(s) of the invalid object as an unacceptable valid object parameter(s).

According to a sixth embodiment of this invention there is provided a method for determining a measurement parameter(s) of a valid object and determining a measurement parameter(s) of an invalid object, comprising:

steps (a) to (g) of the first embodiment; and, (I) on determining a valid object, (h') determining the measurement parameter(s) of the valid object as an acceptable valid object parameter(s);

(II) on determining an invalid object, (h") determining the measurement parameter(s) of the invalid object as an unacceptable valid object parameter(s).

According to a seventh embodiment of this invention there is provided a method for determining a measurement parameter(s) of a valid object and determining a first parameter(s) of a valid object, comprising:

steps (a) to (g) of the first embodiment; and,
on determining a valid object, (h') determining the measurement parameter(s) of the valid object as an acceptable valid object parameter(s);

(i') determining the first parameter(s) of the object from the measurement parameter(s);

(j') determining the first parameter(s) of the valid object as acceptable valid object parameter(s).

According to a eighth embodiment of this invention there is provided a method for determining a measurement parameter(s) and a first parameter(s) of a valid object and determining a measurement parameter(s) of an invalid object, comprising:

steps (a) to (g) of the first embodiment; and, (I) on determining a valid object, (h') determining the measurement parameter(s) of the valid object as an acceptable valid object parameter(s);

(i') determining the first parameter(s) of the object from the measurement parameter(s);

(j') determining the first parameter(s) of the valid object as an acceptable valid object parameter(s);

(II) on determining an invalid object, (h") determining the measurement parameter(s) of the invalid object as an unacceptable valid object parameter(s).

According to a ninth embodiment of this invention there is provided a method for determining a measurement parameter(s) of a valid object and determining a first parameter(s) of an invalid object, comprising:

steps (a) to (g) of the first embodiment; and, (I) on determining a valid object, (h') determining the measurement parameter(s) of the valid object as an acceptable valid object parameter(s);

(II) on determining an invalid object, (i") determining the first parameter(s) of the object from the measurement parameter(s);

(j") determining the first parameter(s) of the invalid object as an unacceptable valid object parameter(s).

According to a tenth embodiment of this invention there is provided a method for determining a first parameter(s) of a valid object and determining a measurement parameter(s) of an invalid object, comprising:

steps(a) to(g) of the first embodiment; and, (I) on determining a valid object.

(i') determining the first parameter(s) of the object from the measurement parameter(s);

(j') determining the first parameter(s) of the valid object as an acceptable valid object parameter(s).

(II) on determining an invalid object, (h") determining the measurement parameter(s) of the invalid object as an unacceptable valid object parameter(s).

According to an eleventh embodiment of this invention there is provided a method for determining a first parameter(s) of a valid object and determining a first parameter(s) of an invalid object, comprising:

steps(a) to (g) of the first embodiment; and, (i) determining the first parameter(s) of the object from the measurement parameter(s);

(I) on determining a valid object, (j') determining the first parameter(s) of the valid object as an acceptable valid object parameter(s).

(II) on determining an invalid object, (j") determining the first parameter(s) of the invalid object as an unacceptable valid object parameter(s).

Generally, the method of the first embodiment further includes at least one of the following steps in an appropriate workable sequence:

(i) determining the first parameter(s) of the object from the measurement parameter(s);

(k) storing the measurement parameter(s) of the object;

(l) storing the first parameter(s) of the object;

(m) retrieving the measurement parameter(s) of the object;

(n) retrieving the first parameter(s) of the object;

(o) storing the validating parameter(s) of the object;

(p) retrieving the validating parameter(s) of the object;

(q) storing the object validation;

(r) retrieving the object validation;

(h') determining the measurement parameter(s) of the valid object as an acceptable valid object parameter(s).

(i') determining the first parameter(s) of the valid object from the measurement parameter(s);

(j') determining the first parameter(s) of the valid object as an acceptable valid object parameter(s);

(k') storing the measurement parameter(s) of the valid object;

(l') storing the first parameter(s) of the valid object;

(m') retrieving the measurement parameter(s) of the valid object;

(n') retrieving the first parameter(s) of the valid object;

(h") determining the measurement parameter(s) of the invalid object as an unacceptable valid object parameter(s).

(i") determining the first parameter(s) of the invalid object from the measurement parameter(s);

(j") determining the first parameter(s) of the invalid object as an unacceptable valid object parameter(s);

(k") storing the measurement parameter(s) of the invalid object;

(l") storing the first parameter(s) of the invalid object;

(m") retrieving the measurement parameter(s) of the invalid object;

(n") retrieving the first parameter(s) of the invalid object.

Generally, the validating energy beam(s) is the same as the measurement energy beam(s) and is an expanding beam of light emerging from a pinhole illuminated by a collimated light beam or is a collimated light beam;

the validation interaction volume(s) is the same as the measurement interaction volume(s) and is one interaction volume;

the validating parameter(s) is the intensity from at least part of an image of the interaction volume produced using the validating outgoing energy, the validating outgoing energy being in the form of light; and the measurement parameter(s) is the intensity of at least a portion of the measurement outgoing energy said measurement outgoing energy being a diffraction pattern produced by light not occluded by the object.

Typically the light beam is a laser light beam.

The methods may include the step of focussing outgoing energy originating from the energy beams in the interaction volumes to provide at least one image of at least a portion(s) of the interaction volumes in the focal plane(s) which image(s) may be a virtual image(s) or a real image(s), in focus or out of focus.

In the first to eleventh embodiments the validating and measurement interaction volume(s) may be the same interaction volume(s), include portions of the same interaction volume(s), or be different interaction volume(s).

If the validating interaction volume(s) is the same as the measurement interaction volume(s) then the step of determining that an object that interacted with the validating energy beam(s) in the validating interaction volume(s) to give rise to the validating outgoing energy from which the validating parameter(s) was detected is in a measurement interaction volume(s), may be the same as determining from the validating parameter(s) whether the validating outgoing energy originated from an interaction between a valid object and the validating beam(s) in the validating volume(s).

In the first to eleventh embodiments the validating and measurement energy beam(s) may be the same energy beam(s), include portions of the same energy beam(s), or be different energy beam(s).

Each of the methods of the first to eleventh embodiments may be repeated a plurality of times and may include:

determining statistical information in respect of a plurality of the measurement parameter(s) and/or the first and/or the validating parameter(s) and/or object validation.

The methods of the first to eleventh embodiments may further comprise:

outputting and/or discarding invalid and/or valid first parameter(s) and/or validating parameter(s) and/or measurement parameter(s) and/or the determination from the validating parameter(s) whether the validating outgoing energy originated from an interaction between a valid object and the validating beam(s) in the validating volume(s).

The method of the first to eleventh embodiments may include:

passing an object through the validating and measurement volume(s).

Generally, the validating energy beam(s) is the same as the measurement energy beam(s) and is an expanding beam of light emerging from a pinhole illuminated by a collimated light beam or is a collimated light beam;

the validation interaction volume(s) is the same as the measurement interaction volume(s) and is one interaction volume;

the validating parameter(s) is the intensity from at least part of an image of the interaction volume produced using the validating outgoing energy, the validating outgoing energy being in the form of light;

the measurement parameter(s) is the intensity of at least a portion of the measurement outgoing energy said measurement outgoing energy being a diffraction pattern;

a valid object comprises a fibre selected from the group consisting of a sheep wool fibre and goat hair; and has a preselected length in a preselected position and orientation in the validation and measurement interaction volume(s) and the first parameter(s) is the diameter of the fibre.

According to a twelfth embodiment of this invention there is provided an apparatus for determining a measurement parameter(s) of an object and whether the object is a valid object, comprising:

(a) a validating energy source(s) for passing a validating energy beam(s) through a validating interaction volume(s);

(b) a validating detector(s) for detecting validating outgoing energy originating from the validating energy beam(s) in the validating interaction volume(s), the detection being in at least one validating focal plane of the validating outgoing energy with respect to the validating interaction volume(s) and means for determining a validating parameter(s) from the detected validating outgoing energy operatively associated with the validating detector(s), the validating detector(s) being operatively associated with the validating energy source(s);

(c) verification means for determining from the validating parameter(s) whether the validating outgoing energy originated from an interaction between an object and the validating beam(s) in the validating volume(s) the verification means being operatively associated with the validating detector(s);

(d) means for locating the object of (c) in a measurement interaction volume(s) the means for locating being operatively associated with the verification means;

(e) a measurement energy source(s) for passing a measurement energy beam(s) through the measurement interaction volume(s) to interact with the object so as to produce measurement outgoing energy;

(f) a measurement detector(s) for detecting at least a portion of the measurement outgoing energy in at least one measurement focal plane of the measurement outgoing energy with respect to the measurement interaction volume(s), the measurement focal plane being different from the validating focal plane, and means for determining a measurement parameter(s) from the detected measurement outgoing energy operatively associated with the measurement detector(s), the measurement detector(s) being operatively associated with the measurement energy source(s); and (g) means for determining from the validating parameter(s) whether the object is a valid object, the means for determining being operatively associated with the validating detector(s).

According to a thirteenth embodiment of this invention there is provided an apparatus for determining a validating parameter(s) and a first parameter(s) of an object, comprising:

the apparatus of the twelfth embodiment; and, means for determining the first parameter(s) of the object from the measurement parameter(s), operatively associated with the measurement detector(s).

According to a fourteenth embodiment of this invention there is provided an apparatus for determining a first parameter(s) of a valid object, comprising:

the apparatus of the twelfth embodiment;

means for determining the first parameter(s) of the valid object from the measurement parameter(s) and for determining the first parameter(s) of the valid object as an acceptable valid object parameter(s), operatively associated with the measurement detector(s) and the means for determining from the validating parameter(s) whether the object is a valid object.

According to a fifteenth embodiment of this invention there is provided an apparatus for determining a measurement parameter(s) of a valid object, comprising:

the apparatus of the twelfth embodiment;

means for determining the measurement parameter(s) of the valid object as an acceptable valid object parameter(s), operatively associated with the measurement detector(s) and the means for determining from the validating parameter(s) whether the object is a valid object.

According to a sixteenth embodiment of this invention there is provided an apparatus for determining a measurement parameter(s) of an invalid object, comprising:

the apparatus of the twelfth embodiment;

means for determining the measurement parameter(s) of the invalid object as an unacceptable valid object parameter(s), operatively associated with the measurement detector(s) and the means for determining from the validating parameter(s) whether the object is a valid object.

According to a seventeenth embodiment of this invention there is provided an apparatus for determining a first parameter(s) of an object and determining a first parameter(s) of an invalid object, comprising:

the apparatus of the twelfth embodiment;

means for determining the first parameter(s) of the object from the measurement parameter(s) and for determining the first parameter(s) of the invalid object as an unacceptable valid object parameter(s), operatively associated with the measurement detector(s) and the means for determining from the validating parameter(s) whether the object is a valid object.

According to a eighteenth embodiment of this invention there is provided an apparatus for determining a measurement parameter(s) of a valid object and determining a measurement parameter(s) of an invalid object, comprising:

the apparatus of the twelfth embodiment;

means for determining the measurement parameter(s) of the valid object as an acceptable valid object parameter(s) and for determining the measurement parameter(s) of the invalid object as an unacceptable valid object parameter(s), operatively associated with the measurement detector(s) and the means for determining from the validating parameter(s) whether the object is a valid object.

According to a nineteenth embodiment of this invention there is provided an apparatus for determining a measurement parameter(s) of a valid object and determining a first parameter(s) of a valid object, comprising:

the apparatus of the twelfth embodiment;

means for determining the measurement parameter(s) of the valid object as an acceptable valid object parameter(s) and for determining the first parameter(s) of the object from the measurement parameter(s) and for determining the first parameter(s) of the valid object as acceptable valid object parameter(s), operatively associated with the measurement detector(s) and the means for determining from the validating parameter(s) whether the object is a valid object.

According to a twentieth embodiment of this invention there is provided an apparatus for determining a measurement parameter(s) and a first parameter(s) of a valid object and determining a measurement parameter(s) of an invalid object, comprising:

the apparatus of the twelfth embodiment;

means for determining the measurement parameter(s) of the valid object as an acceptable valid object parameter(s) and for determining the first parameter(s) of the object from the measurement parameter(s) and for determining the first parameter(s) of the valid object as an acceptable valid object parameter(s) and for determining the measurement parameter(s) of the invalid object as an unacceptable valid object parameter(s), operatively associated with the measurement detector(s) and the means for determining from the validating parameter(s) whether the object is a valid object.

According to a twenty first embodiment of this invention there is provided an apparatus for determining a measurement parameter(s) of a valid object and determining a first parameter(s) of an invalid object, comprising:

the apparatus of the twelfth embodiment;

means for determining the measurement parameter(s) of the valid object as an acceptable valid object parameter(s) and for determining the first parameter(s) of the object from the measurement parameter(s) and for determining the first parameter(s) of the invalid object as an unacceptable valid object parameter(s), operatively associated with the measurement detector(s) and the means for determining from the validating parameter(s) whether the object is a valid object.

According to a twenty second embodiment of this invention there is provided an apparatus for determining a first parameter(s) of a valid object and determining a measurement parameter(s) of an invalid object, comprising:

the apparatus of the twelfth embodiment;

means for determining the first parameter(s) of the object from the measurement parameter(s) and for determining the first parameter(s) of the valid object as an acceptable valid object parameter(s) and for determining the measurement parameter(s) of the invalid object as an unacceptable valid object parameter(s), operatively associated with the measurement detector(s) and the means for determining from the validating parameter(s) whether the object is a valid object.

According to a twenty third embodiment of this invention there is provided an apparatus for determining a first parameter(s) of a valid object and determining a first parameter(s) of an invalid object, comprising:

the apparatus of the twelfth embodiment;

means for determining the first parameter(s) of the object from the measurement parameter(s) and for determining the first parameter(s) of the valid object as an acceptable valid object parameter(s) and for determining the first parameter(s) of the invalid object as an unacceptable valid object parameter(s), operatively associated with the measurement detector(s) and the means for determining from the validating parameter(s) whether the object is a valid object.

Generally, the apparatus of the twelfth embodiment further comprises at least one of the following items:

(i) means for determining the first parameter(s) of the object from the measurement parameter(s) operatively associated with the measurement detector(s);

(k) means for storing the measurement parameter(s) of the object operatively associated with the measurement detector(s);

(l) means for storing the first parameter(s) of the object operatively associated with the means for determining the first parameter(s);

(m) means for retrieving the measurement parameter(s) of the object operatively associated with the means for storing the measurement parameter(s);

(n) means for retrieving the first parameter(s) of the object operatively associated with the means for storing the first parameter(s);

(o) means for storing the validating parameter(s) of the object operatively associated with the validating detector(s);

(p) means for retrieving the validating parameter(s) of the object operatively associated with the means for storing the validating parameter(s);

(q) means for storing the object validation operatively associated with the means for determining whether the object is a valid object;

(r) means for retrieving the object validation operatively associated with the means for storing the object validation;

(h') means for determining the measurement parameter(s) of the valid object as an acceptable valid object parameter(s) operatively associated with the means for determining whether the object is a valid object and the measurement detector(s);

(i') means for determining the first parameter(s) of the valid object from the measurement parameter(s) operatively associated with the means for determining whether the object is a valid object and the measurement detector(s);

(j') means for determining the first parameter(s) of the valid object as an acceptable valid object parameter(s) operatively associated with the means for determining whether the object is a valid object and the means for determining the first parameter(s) of the valid object(or the object);

(k') means for storing the measurement parameter(s) of the valid object operatively associated with the means for determining whether the object is a valid object and the measurement detector(s);

(l') means for storing the first parameter(s) of the valid object operatively associated with the means for determining whether the object is a valid object and the means for determining the first parameter(s) of the valid object(or the object);

(m') means for retrieving the measurement parameter(s) of the valid object operatively associated with the means for determining whether the object is a valid object and the means for storing the measurement parameter(s) of the valid object (or the object);

(n') means for retrieving the first parameter(s) of the valid object operatively associated with the means for determining whether the object is a valid object and the means for storing the first parameter(s) of the valid object(or the object);

(h") means for determining the measurement parameter(s) of the invalid object as an acceptable invalid object parameter(s) operatively associated with the means for determining whether the object is a invalid object and the measurement detector(s);

(i") means for determining the first parameter(s) of the invalid object from the measurement parameter(s) operatively associated with the means for determining whether the object is a invalid object and the measurement detector(s);

(j") means for determining the first parameter(s) of the invalid object as an acceptable invalid object parameter(s) operatively associated with the means for determining whether the object is a invalid object and the means for determining the first parameter(s) of the invalid object(or the object);

(k") means for storing the measurement parameter(s) of the invalid object operatively associated with the means for determining whether the object is a invalid object and the measurement detector(s);

(l") means for storing the first parameter(s) of the invalid object operatively associated with the means for determining whether the object is a invalid object and the means for determining the first parameter(s) of the invalid object(or the object);

(m") means for retrieving the measurement parameter(s) of the invalid object operatively associated with the means for determining whether the object is a invalid object and the means for storing the measurement parameter(s) of the invalid object(or the object);

(n") means for retrieving the first parameter(s) of the invalid object operatively associated with the means for determining whether the object is a invalid object and the means for storing the first parameter(s) of the invalid object (or the object).

The means for determining, storing and retrieving the measurement parameter(s) and/or the first parameter(s) may perform such a step(s) prior to or after the determination of the validity of an object.

Advantageously, the validating energy source(s) is the same as the measurement energy source(s);

the validating energy beam(s) is the same as the measurement energy beam(s) and is an expanding beam of light emerging from a pinhole illuminated by a collimated light beam or is a collimated light beam;

the validation interaction volume(s) is the same as the measurement interaction volume(s) and is one interaction volume; and the validating parameter(s) is the intensity from at least part of an image of the interaction volume produced using the validating outgoing energy, the validating outgoing energy being in the form of light; and the measurement parameter(s) is the intensity of at least a portion of the measurement outgoing energy said measurement outgoing energy being a diffraction pattern.

Generally, the validating energy source(s) is the same as the measurement energy source(s);

the validating energy beam(s) is the same as the measurement energy beam(s) and is an expanding beam of light emerging from a pinhole illuminated by a collimated light beam or is a collimated light beam;

the validation interaction volume(s) is the same as the measurement interaction volume(s) and is one interaction volume;

the validating parameter(s) is the intensity from at least part of an image of the interaction volume produced using the validating outgoing energy, the validating outgoing energy being in the form of light;

the measurement parameter(s) is the intensity of at least a portion of the measurement outgoing energy said measurement outgoing energy being a diffraction pattern;

a valid object comprises a fibre selected from the group consisting of a sheep wool fibre and goat hair; and has a preselected length in a preselected position and orientation in the validation and measurement interaction volume(s) and the first parameter(s) is the diameter of the fibre.

Typically, the apparatus further comprises means for determining statistical information in respect of a plurality of the diameters of the valid object(s).

Typically, the validating outgoing energy is light; and the apparatus further comprises a light focuser to form an image of the validating interaction volume on the validating detector(s), operatively associated with the validating source(s) and validating detector(s).

Typically, the measurement outgoing energy is light; and the apparatus further comprises a light focuser to form an image of the measurement interaction volume on the measurement detector(s), operatively associated with the measurement source(s) and measurement detector(s).

Advantageously, the apparatus of the invention may further comprise:

means to pass an object through the measurement and validating interaction volumes, operatively associated with the validating energy source(s), measurement energy source(s) and the means for locating.

Typically the light source is a laser.

The apparatus may include a focuser(s) for focussing outgoing energy originating from the energy beams in the interaction volumes to provide at least one image of at least a portion(s) of the interaction volumes in the focal plane which image(s) may be a virtual image(s) or a real image(s), in focus or out of focus at the validating detector(s) and/or the measurement detector(s).

The validating and measurement means may be the same, may include common elements or may be different from one another.

The validating and measurement energy sources may be the same, may include common elements or may be different from one another.

The measurement parameter(s) and validating parameter(s) may be the same or may be different from one another. If they are the same they may differ in that they are detected at different precisions, for example. The measurement parameter(s) and validating parameter(s) may both be used to determine the first parameter(s) and/or the object validation(but to different resolutions from one another).

The measurement and validating detector(s) may be the same, may include common elements or may be different from one another.

The detection of the validating and measurement outgoing energies may take place simultaneously, at overlapping times or at different times and/or the measurement parameter(s) may be used to determine the validity of the measurement and/or the validating parameter(s) may be used to determine the first parameter(s).

The validating and measurement interaction volume(s) may be the same interaction volume(s), include portions of the same interaction volume(s), or be different interaction volume(s).

The validating and measurement energy beam(s) may be the same energy beam(s), include portions of the same energy beam(s), or be different energy beam(s).

The apparatus of the invention may further comprise:

means for outputting and/or discarding invalid and/or valid first parameter(s) and/or validating parameter(s) and/or measurement parameter(s) and/or the determination from the validating parameter(s) whether the validating outgoing energy originated from an interaction between a valid object and the validating beam(s) in the validating volume(s), the means for outputting being operatively associated with the means for determining the first and/or validating parameter(s) and/or the means for storing the measurement parameter(s) and/or the first and/or validating parameter(s) and/or the validating and/or measurement detector(s).

The outputting may be in the form of an information signal or information display, for example. Examples of information signals or information displays include written text, on paper, electronic display screens (LCD screens, electroluminescent screens, gas plasma screens, video monitors, for example) digital or analogue electronic signals, acoustic signals, magnetic signals, electromagnetic signals, for example.

The apparatus of the invention may include:

means for determining statistical information in respect of a plurality of measurement and/or first and/or validating parameter(s), and/or object validations operatively associated with the means for determining the first and/or validating parameter(s) and/or the means for storing the measurement parameter(s) and/or the first and/or validating parameter(s) and/or the validating and/or measurement detector(s).

Examples of statistical information include mean, standard deviation, coefficient of variation, variance, skewness, kurtosis, and other moments about the mean, spline fits, line fits including linear, exponential, logarithmic, multiple and polynomial regressions, fractal fitting, mode, median, distribution fits including normal, gaussian, fermi, poisson, binomial, Weibull, parabolic, frequency, probability, cumulative and top hat distributions, data smoothing including running medians, means and least squares, table formation such as histograms and two way contingency, data manipulation for graphs, forecasting, probability statistics, simulations, pattern recognition, t test, chi square test, sample size, Wilcoxon signed-rank test, rank sum test, Kolmogorov-Smirnov test and boundary value and limit statistics. A more detailed description of statistical techniques is disclosed in G. E. P. Box, W. G. Hunter and J. S. Hunter, Statistics for Experimenters, John Wiley & Sons, Inc, New York, U.S.A., 1978, the contents of which are incorporated herein by cross reference.

Generally, multiple focal planes of the outgoing energies are detected.

A valid object must have a measurable parameter(s) which can be validated. Examples of such measurable parameter(s) include a valid shape, diameter, area, chemical composition, colour, number of parts, thickness, width, length, absorptivity, reflectivity, transmittivity, dielectric constant, Raman scattering profile, fluorescence, surface texture or other surface detail, position, orientation, surface tension, surface roughness, surface profile or density, for example in the ease of a fibrous object for example where the first parameter is diameter, for example a valid object may be one in which a single fibre fully traverses the centre of the validating and measurement beam(s)(which may be the same beam) in the validating and measurement volume(s)(which may be the same volume).

The first parameter(s) may be shape, diameter, area, chemical composition, colour, number of parts, thickness, width, length, absorptivity, reflectivity, transmittivity, dielectric constant, Raman scattering profile, fluorescence, surface texture or other surface detail, position, orientation, surface tension, surface roughness, surface profile or density, for example. In the case of a fibrous object for example the first parameter may be diameter, for example.

A valid first parameter(s) measuring position and orientation may be when an object fully crosses the centre of the energy beam(s) and without another object being in the energy beam(s). The validation may be false if there is no object in the interaction volume(s) or if there is more than one object in the energy beam(s) in the interaction volume(s) or if the object does not intersect the energy beam(s) fully in the interaction volume(s) or if the object in the energy beam(s) in the interaction volume(s) is not a single bodied object, for example.

The energy source(s) may be coherent, partially coherent or incoherent and can provide a solid particle beam, such as a neutron, proton or electron beam or a beam of alpha particles, acoustic waves, such as sound waves, or electromagnetic radiation, such as gamma rays, x-rays, UV light, visible light, infrared light or microwaves. Generally the energy source is a source of electromagnetic radiation with a wavelength in the range of and including far IJV to far IR.

Examples of light sources include incandescent sources, such as tungsten filament source, vapour lamps such as halogen lamps including sodium and iodine vapour lamps, discharge lamps such as xenon arc lamp and a Hg are lamp, solid state light sources such as photo diodes, super radiant diodes, light emitting diodes, laser diodes, electroluminescent light sources, frequency doubled lasers, laser light sources including rare gas lasers such as an argon laser, argon/krypton laser, neon laser, helium neon laser, xenon laser and krypton laser, carbon monoxide and carbon dioxide lasers, metal ion lasers such as cadmium, zinc, mercury or selenium ion lasers, lead salt lasers, metal vapour lasers such as copper and gold vapour lasers, nitrogen lasers, ruby lasers, iodine lasers, neodymium glass and neodymium YAG lasers, dye lasers such as a dye laser employing rhodamine, 640, Kiton Red 620 or rhodamine 590 dye, and a doped fibre laser.

The energy source may be a pinhole energy source. The energy source may comprise an energy fibre, the exit end of which may effectively act as a pinhole source.

The energy beam(s) may be collimated, diverging or converging.

The energy beam(s) in the interaction volume(s) may take the form of a diffraction pattern(s).

The outgoing energy may be transmitted and/or redirected energy.

The outgoing energy may include an interacted and/or uninteracted portion of the energy beam(s).

The outgoing energy where it intersects the validation detector may be a portion of the diffraction pattern resulting from the occlusion of the energy beam(s) by a portion of an object in the interaction volume(s).

If the source is a pinhole source and the energy beam(s) is the diffraction pattern resulting from the passage of energy through the pinhole, the outgoing energy in a focal plane may take the form of the optical superposition of the diffraction pattern resulting from the pinhole and the diffraction pattern resulting from interaction between the energy beam(s) and a portion of the object in the interaction volume(s).

The apparatus may include means to pass the object through the interaction volume(s), the means to pass being operatively associated with the means for locating. The means to pass may be a sample carrier such as a conveyer strip, a sample holder on a linear or rotary stage or a fluid stream (fluid including liquids and gases), for example. The fluid stream may be confined by a cell which cell is used to orientate objects therein. The interaction volume(s) may be defined by the intersection of the central portion of the energy beam(s) and the cell. The cell may be of the type described in Australian Patent No. 472,862 the contents of which are incorporated heroin by cross reference and/or Australian Patent No. 599,053 the contents of which are incorporated heroin by cross reference.

The apparatus may comprise a scanner operatively associated with the energy source(s) and/or the object and/or the sample carrier to scan the energy beam relative to the object in the interaction volume(s). The scanner may be a piezoelectric stack, a magnetic core/magnetic coil combination, a mechanical vibrator, an electromechanical vibrator, a mechanical or electromechanical scanning mechanism such as a servomotor, an acoustic coupler electrooptic scanning means or any other suitable means.

The energy source(s) may include a first energy deflector located between the source and the interaction volume(s) wherein a portion of the energy beam(s) passes through the first deflector and whereby the first deflector is operatively associated with the source to alter the shape, size, wavelength, intensity, polarisation, phase, direction of travel or focus of at least a portion of the energy beam(s) in the interaction volume(s).

There may be disposed in the path of the outgoing energy between the interaction volume(s) and the validation detector and/or the measurement detector, a second energy deflector wherein the outgoing energy passes through the second deflector which alters the size, shape, intensity, polarisation, phase, direction of travel, focus or wavelength, for example. The second energy deflector may split the validating and measurement outgoing energy.

The first and second energy deflectors may include energy focusers or energy reflectors.

The focuser may be refractive lenses, including microscope objectives, reflective lenses, and/or holographic optical elements. If the energy is of a frequency other than in the range of UV to near infrared light or other types of energies, analogous focussing elements are used in place of the optical focussing elements.

The reflector may be a mirror or partially silvered mirror, a beam splitter including a polarisation dependent beam splitter, energy waveguide splitter (eg an optical fibre coupler) or a wavelength dependent beam splitter, for example. The optical fibre coupler may be a fused biconical taper coupler, a polished block coupler, a bottled and etched coupler or a bulk optics type coupler with fibre entrance and exit pigtails, a planar waveguide device based on photolithographic or ion-diffusion fabrication techniques or other like coupler.

The object may be a fluid or solid or other of matter. Examples of objects include mineral objects, such as diamonds and other crystals, organic and inorganic contaminants, fibrous objects, randomly shaped objects, spherical objects or cylindrical objects. Generally the objects are fibrous objects or woven or twisted fibrous objects. The fibrous objects may be synthetic fibres or natural fibres. The fibres may be fibreglass fibres, hessian fibres, nylon fibres, glass fibres, polnosic and polyester fibres, abaca fibres, silk fibres, jute fibres, flax and cellulose fibres (including paper, recycled paper, corn stalks, sugar cane, wood, wood shavings, bagasse, wood chips), regenerated fibres such as viscose, rayon, cuprammonium rayon and cellulose acetate, sisal fibres, carbon fibres, stainless steel fibres, vegetable fibrous material, polyolefin fibres such as polyethylenes and polypropylene, steel fibres, boron fibres, copper fibres, brass fibres, teflon fibres, dacron fibres, mylar fibres, aluminium fibres, aluminium alloy fibres, polyamide fibres, polyacrylic fibres, or absorbent fibres such as nylon 66 polyacrylonitrile, or polyvinyl alcohol and absorbent types of polyesters or polyacrylics, edible vegetable fibres, such as wheat fibres, or inedible vegetable fibres, such as wood pulp or cotton fibres, animal fibres, such as meat fibres, wool fibres such as wool fibres from sheep, hairs, such as human hairs, goat hairs, cattle hairs, or feathers, yarns including wool and cotton yarns, string, wire, optical fibres for example.

Typically, a valid object comprises a fibre selected from the group consisting of a fibreglass fibre, hessian fibre, nylon fibre, glass fibre, polnosic fibre, polyester fibre, abaca fibre, silk fibre, jute fibre, flax fibre, cellulose fibre, regenerated fibre, sisal fibre, carbon fibre, stainless steel fibre, vegetable fibre, polyolefin fibre, steel fibre, boron fibre, copper fibre, brass fibre, teflon fibre, dacron fibre, mylar fibre, aluminium fibre, aluminium alloy fibre, polyamide fibre, polyacrylic fibre, nylon 66 polyacrylonitrile fibre, polyvinyl alcohol fibre, edible vegetable fibre, inedible vegetable fibre, wood pulp fibre, cotton fibre, animal fibre, meat fibre, sheep wool fibre, hair, human hair, goat hair, cattle hair, yarn, wool yarn, cotton yarn, string, wire and optical fibre.

Generally, a valid object has a preselected length in a preselected position and orientation in the validation and measurement interaction volume(s).

The measurement and/or validation detector(s) may comprise an array of detecting elements and/or apertures. An aperture in the array may be an energy entrance portion of an energy guide operatively associated with the validating and/or measurement focal plane(s) to collect a portion of the outgoing energy and guide it to the measurement and/or validation detector(s). A detecting element in the array may be photodiode, photomultiplier, part of a ccd array or the like.

The array may be a three dimensional array or a planar array.

The outgoing energy may be a beam and the array may be symmetric about the central axis of the beam. The array may be a linear, square, rectangular, circular, hexagonal, spiral, spherical, cubic or random array, for example. Some of the apertures or detecting elements in the array may be elongated, round, elliptical, square, rectangular, triangular, hexagonal, rhomboid or random in shape, for example.

The apertures or detecting elements may be movable or fixed with respect to the validating focal plane and/or the measurement focal plane and/or the measurement and/or validating interaction volume(s).

The energy guide may be a slab waveguide. The slab waveguide can be a single mode slab waveguide.

The energy guide can be an energy fibre.

The energy guide can be a multi mode optical fibre.

The energy guide can be a single mode optical fibre. For example, a four micron core fibre which is single mode at a wave length of 633 nanometers given an appropriate refractive index profile. A step index optical fibre becomes single mode when the numerical aperture, NA, the fibre core radius, a, and the wave length of light, $\lambda$, obey the relationship:

$$2 \times \pi \times NA \times a / \lambda \leq 2.405,$$

more typically $$2 \times \pi \times NA \times a / \lambda \leq 0.6.$$

The energy guide may be a fibre bundle.

The optical fibres may include glass or plastic elements or a combination of these.

Portions of the source and detector energy guides may be portions of the same energy guide.

The validating detector(s) and/or the measurement detector(s) may comprise an array of detecting elements.

When the validating outgoing energy is light the validating detector(s) may comprise an optical fibre(s) coupled to a detecting element(s).

When the measurement outgoing energy is light the measurement detector(s) may comprise an optical fibre(s) coupled to a detecting element(s).

The validating detector(s), the measurement detector(s), the means to determine the first parameter(s), and/or validating means and/or means for locating may comprise a calculator which may include optical, electrical, optoelectronic, mechanical or magnetic elements, for example, or may include such techniques as optical and/or electrical heterodyning, quadrature operation, multi area detectors or phase lock loop techniques, for example. The means for determining the first parameter(s) may log and analyse a signal(s) from the measurement detector(s) and/or validation detector(s) or may log and analyse the first parameter(s) and/or validating parameter(s) and/or the measurement parameter(s) and/or the object validation. The means for determining the first parameter(s) typically includes a computer.

The means for locating may comprise a timer and/or a counter.

The interaction is typically one or a combination of refraction, diffraction, reflextion, scattering, fluorescence, stimulated emission, incandescence, shadowing, polarisation rotation, phase retardation and other polarisation effects, occlusion, optical absorption, interference effects, sum frequency generation, one giving rise to a diffraction pattern, refraction, phase alteration, second, third or fourth harmonic generation, difference frequency generation, optical bistability, self bleaching, Raman scattering or Brillouin scattering. A nonlinear reaction can be involved as a result of heating, refractive index change, charge build-up or charge migration.

The first parameter(s) and the measurement parameter(s) may be the same or may include some of the same elements or they may be different from one another.

The validating parameter(s) and the measurement parameter(s) may be energy intensity(including spatially or temporally dependent intensity patterns such as images or intensity peaks or troughs as or not as a function of time), amplitude, wavelength or frequency modulation, phase, polarisation, wavelength, direction of travel, for example.

The apparatus of the invention may include:

a mask to mask off a portion of the validating and/or measurement and/or validating outgoing and/or measurement outgoing beams.

For the purposes of this specification planes of focus include diffraction planes at different distances from an object whether real or apparent(as a result of a focuser, for example). Note that an in focus image of an object is the diffraction plane in the plane of the object, but may be magnified or reduced. Note also that a focuser may be used to create a virtual as opposed to a real image.

BEST MODE AND OTHER MODES FOR CARRYING OUT THE INVENTION

Figure 1:
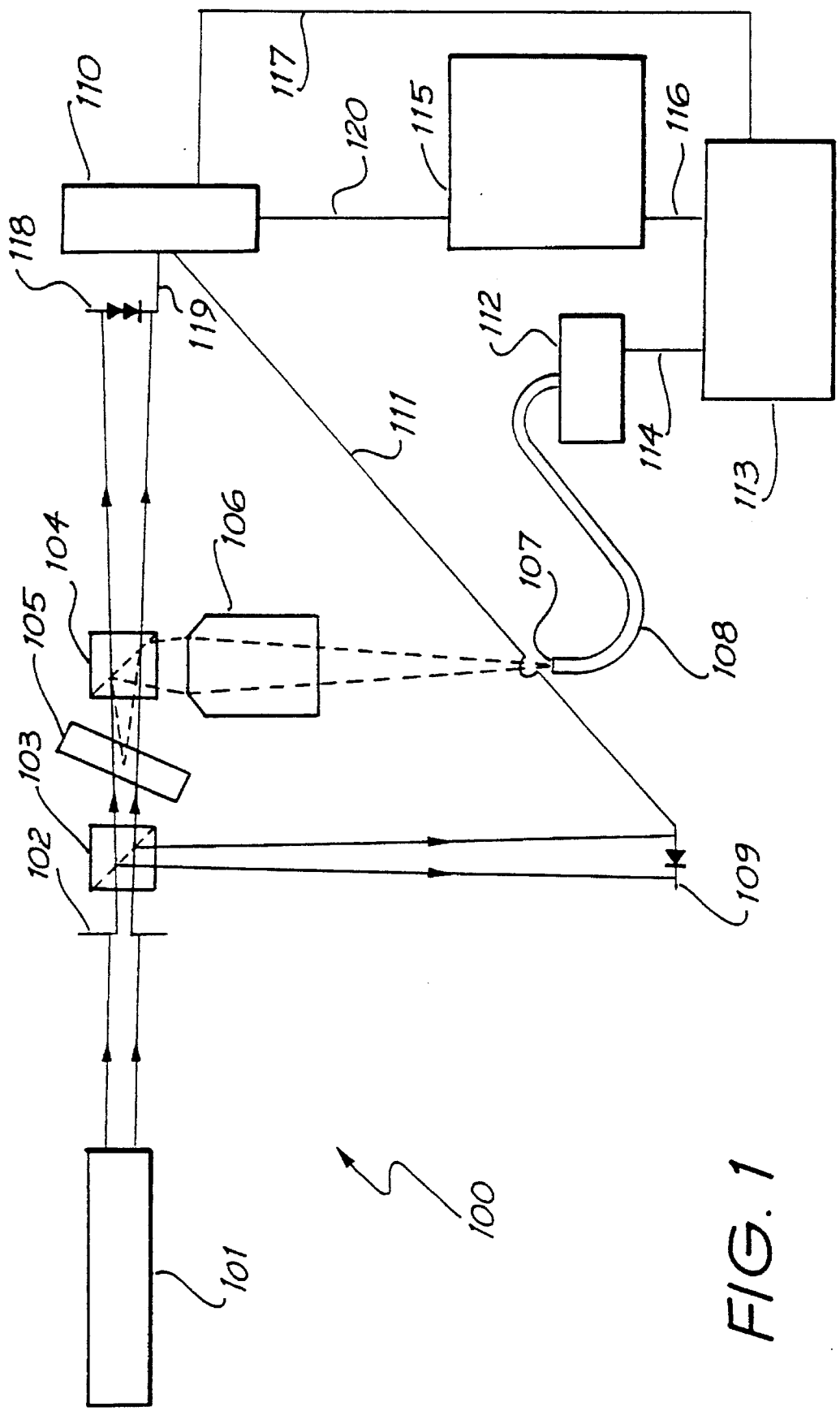
FIG. 1 schematically depicts an apparatus for determining a the mean and standard deviation of a plurality of diameters of wool fibres, in accordance with the invention.

Referring to FIG. 1 an apparatus 100 for determining the mean and standard deviation of a plurality of diameters of wool fibres, includes a validating and a measurement laser light source, namely He-Ne laser 101, and a 276 micrometer diameter pinhole 102 which form a pinhole diffraction validating and measurement expanding laser beam which passes through a validating and measurement interaction volume defined by the intersection of the central diffraction spot and first diffraction ring of the expanding laser beam and tapered cell 105 oriented not normal to the direction of travel of the expanding laser beam. The optical path length between the center of cell 105 and pinhole 102 is 90 mm. Polarisation independent beam splitter 103 is operatively disposed to pinhole 102 and laser 101 to direct a portion of the expanding laser beam to 1 mm diameter reference detector 109 which is electrically connected to processor 110 via line 111. The optical path length between pinhole 102 and detector 109 is 208 mm. When apparatus 100 is operating wool fibres in an isopropanol-wool slurry pass through cell 105 generally at a non-zero degree angle to the direction of slurry flow through cell 105 to scatter, reflect, diffract, absorb, refract and otherwise interacts with the expanding laser beam in the interaction volume from laser 101. A detailed description of cell 105 is contained in Australian Patent no. 599 053. Polarisation independent beam splitter 104 and microscope objective 106 are operatively disposed with respect to laser 101, pinhole 102 and cell 105 to produce, using validating outgoing light from the interaction volume, an in focus magnified transmission image of wool fibres in the validating and measurement interaction volume in the plane of end 107 of 18 optical fibre ring bundle 108 comprising at end 107 a central fibre surrounded by a 2.597 mm diameter ring of 16 plastic optical fibres each having a 0.5 mm diameter core and a 10 micrometer thick cladding and a single mode fibre. The optical path length between the centre of cell 105 and the front principal plane of objective 106 is 42.4 mm and the optical path length between the back principal plane of objective 106 and end 107 is 228.2 mm so the image from the centre of cell 105 is magnified by 5.4 times at end 107. Each of the plastic fibres in bundle 108 is connected to a photodiode detector in an the array of 17 photodiode detectors comprising validating detector 112 for detecting the light intensity passing through each of the fibres in bundle 108 from validating outgoing energy originating from the validating and measurement beam in the interaction volume. Processor/timer 113 is connected electrically to detector 112 by line 114. Processor/timer 113 is also connected electrically to computer 115 by line 116 and to processor 110 by line 117. One mm diameter split detector 118 is connected electrically to processor 110 by line 119. Processor 110 is connected electrically to computer 115 by line 120. Detector 118 is operatively disposed with respect to laser 101, pinhole 102 and cell 105 to detect measurement outgoing light which is in the form of a diffraction pattern. The optical path length between the centre of cell 105 and detector 118 is 118 mm.

Figure 4:
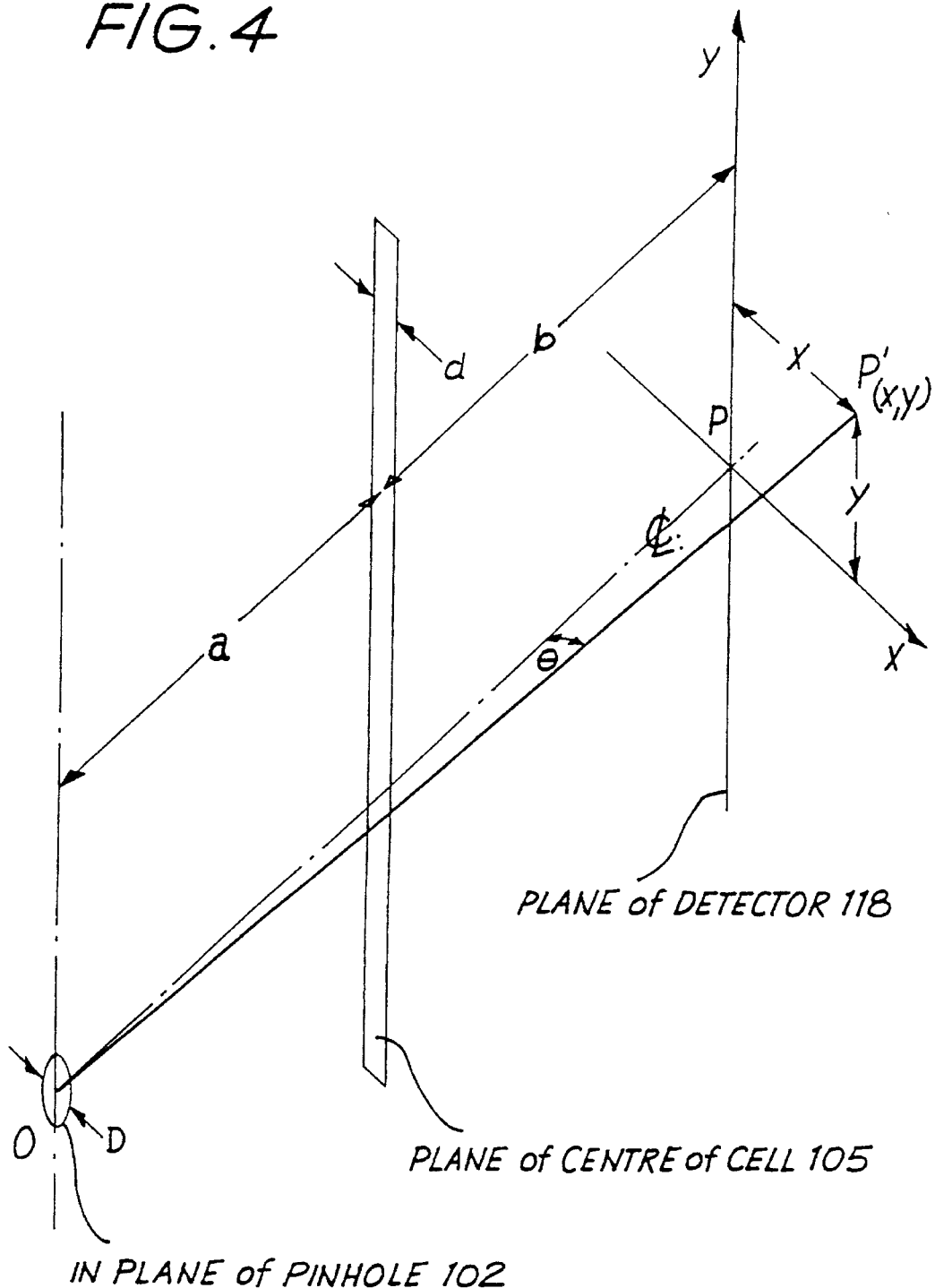
FIG. 4 schematically depicts the geometry for the apparatus of FIG. 1.

Referring to FIG. 4, which schematically depicts the geometry for apparatus 100, the observed diffraction pattern intensity at split detector 118, resulting from pinhole 102 of diameter D and a wool fibre of diameter d at the plane of cell 105 is given by $$I(v) = (\Delta X_{m,l} + \Delta X_{m,u})^2 + (\Delta Y_{m,l} + \Delta Y_{m,u})^2 \quad (1)$$

where $$\Delta X_{m,l} = \int_{-\infty}^{-(v + \Delta v/2)} A(v+p)\cos \pi \cdot p^2/2 \, dp \quad (2)$$

$$\Delta Y_{m,l} = \int_{-\infty}^{-(v + \Delta v/2)} A(v+p)\sin \pi \cdot p^2/2 \, dp \quad (3)$$

$$\Delta X_{m,u} = \int_{-(v - \Delta v/2)}^{\infty} A(v+p)\cos \pi \cdot p^2/2 \, dp, \quad (4)$$

and $$\Delta Y_{m,u} = \int_{-(v - \Delta v/2)}^{\infty} A(v+p)\sin \pi \cdot p^2/2 \, dp \quad (5)$$

In equations (2) to (5) $A(v+p)$ is the illumination field amplitude in the plane of cell 105. The equivalent normalised position on detector 118 is given by $$v = x/\sqrt{[(1+b/a)b.\lambda/2]}, \quad (6)$$

the normalised wool fibre diameter is $$\Delta v = d\sqrt{[2(a+b)/a.b.\lambda]}, \quad (7)$$

a is the optical path length between from pinhole 102 and the centre of cell 105, b is the optical path length between centre of cell 105 and detector 118 and λ is the wavelength of the light from laser 101.

As pinhole 102 is substantially uniformly illuminated by laser light from laser 101, the illumination field amplitude at the plane of the centre of cell 105 is circularly symmetric and is given by $$A(x,y) = 2 J_1(z)/z \qquad (8)$$

where $J_1(z)$ is the first order Bessel function of the first kind and $$z = (\pi.D/(a+b)\lambda).\sqrt{(x^2+y^2)} \qquad (9)$$

To calculate the diffraction pattern intensity $I(v)|_{y=y}$ of equation (1), along any off-axis line y=y, equation (8) is used to calculate the Fraunhofer field amplitude appearing in equations (2)–(5).

In order to obtain geometrically similar configurations of apparatus 100 for different optical systems, the diffraction pattern at detector 118 must scale identically with the change in detector size for the two configurations for any given wool fibre. If the radius of detector 118 for the new apparatus 100 (denoted by dashed variables) is related to the old detector 118 radius R by $$R' = kR \qquad (10)$$

then to get geometric similarity $$b' = kb \qquad (11)$$

$$a' = k.b/[(1+b/a)k-1] \qquad (12)$$

$$D'/D = (a'+b')/(a+b).k \qquad (13)$$

Equations (10), (11), (12) and (13) thus define a new apparatus 100, which is geometrically similar to the old and thus responds in exactly the same way when a wool fibre passes through the interaction volume. For example, suppose apparatus 100 with detector 118 of radius R=0.5 mm, D=276.5 micrometers and with (a,b)=(90,118) mm is replaced with a new detector 118 of radius R'=1 mm. The scaling factor is now k=2 and the new cell 105 and detector 118 planes must be located at (a',b')=(65,235) mm, while the new pinhole 102 diameter is D'=200 micrometers, for the new apparatus 100 to have the same response as the old one.

For the two geometries outlined above, there is an apparent change in wool fibre diameter with the position of the wool fibre along the axis of the expanding laser beam. Thus, because cell 105 has a finite width, typically 2 mm, there is an uncertainty in the measured diameter. This uncertainty is typically +/-1.9% for a 30 micron fibre. However, the apparatus of FIG. 1 may be rescaled so that there is no substantial apparent diameter change with axial position of wool fibres along the axis of the expanding laser beam. This can be done by making a=b or a and b tend to infinity or R tend to 0. Thus, for an arrangement that is geometrically similar to the two described above, one might put a'=b'= 101.9 mm, D'=313.3 micrometers and R'=0.434 mm.

If a substantial amount of interacted light is collected by detector 118, then diameter independent parameters such as wool fibre medulation and colour as well as position and orientation, for example may affect the diameter determination and thus the accuracy of the measurement. Thus in apparatus 100, detector 118 is placed with respect to cell 105 so as to not collect so much light from the interaction volume that has interacted with a wool fibre in cell 105 to prevent determination of the diameter of the wool fibre to within the required accuracy. Detector 118 may be placed closer to cell 105, at the expense of accuracy, but for optimum accuracy should be positioned as far as possible from cell 105 to minimise effects from diameter independent parameters on the wool fibre diameter determination. Because of the nature of the expanding beam from pinhole 102, there is a practical limitation on the upper limit of separation between cell 105 and detector 108. A alternative practical apparatus for measuring fibre diameter independent of wool fibre diameter independent parameters, in which the measurement detector is located at an effective infinite distance from the interaction volume is described below with reference to FIG. 2.

End 107 is centred in the image of the pinhole diffraction in the interaction volume by maximising the light intensity collected by the central fibre. The image of the pinhole diffraction in the interaction volume is bought into focus at end 107 by positioning end 107 so that the light intensity signal collected by the single mode fibre in bundle 108 substantially approximates a top hat profile when a wool fibre passes through cell 105. Generally the fibres in the ring at end 107 are packed closely to one another to minimise the separations between them. The magnification of the interaction volume at end 107 is such that the 16 0.5 mm optical fibres in the ring of bundle 108 at end 107 are located just outside the first minimum of the pinhole diffraction pattern of the image at end 107 to capture light from the first diffraction ring. If different diameter optical fibres are chosen or the number of fibres in the ring is changed, for example, the position of objective 106 with respect to cell 105 and end 107 is adjusted such that the optical fibres in the ring of bundle 108 at end 107 are located just outside the first minimum of the pinhole diffraction pattern of the image at end 107.

Since the image of wool fibres in the interaction volume at end 107 is in focus, information about the position and orientation of the wool fibres is readily obtainable from the image. If end 107 is moved from the position of the in focus image of the interaction volume the position and orientation of the wool fibres may be less readily obtainable.

Figure 5:
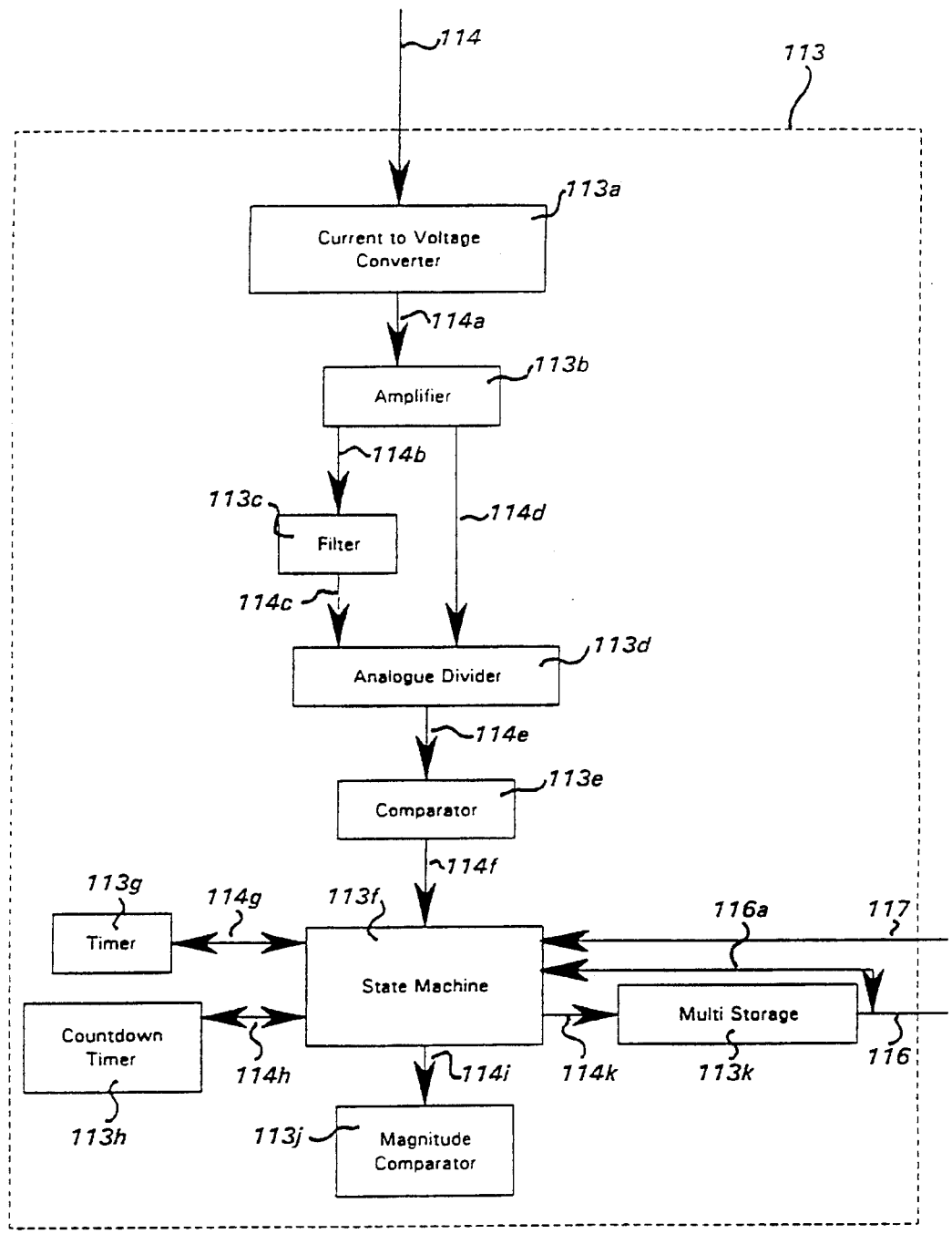
FIG. 5 schematically depicts in detail the processor/timer in the apparatus of FIG. 1.

As depicted schematically in FIG. 5, processor/timer 113 comprises current to voltage converter 113a electrically connected to detector 112 by line 114 and to amplifier 113b by line 114a. Amplifier 113b is electrically connected to three pole butterworth filter 113c via line 114b and analogue divider 113d by line 114d. Analogue divider 113d is also electrically connected to comparator 113e by line 114e and filter 113c via line 114c. Comparator 113e is electrically connected to state machine 113f via line 114f. State machine 113f is identified as a means for locating for determining that the wool fibre that interacted with the expanding laser beam in the interaction volume to give rise to validating outgoing energy is the same wool fibre that gave rise to the measurement outgoing light for the current measurement. State machine 113f is electrically connected to timer 113g via line 114g, countdown timer 113h via line 114h, magnitude comparator 113j via line 114i, multi storage device 113k via line 114k, computer 115 via line 116a and line 116 and processor 110 via line 117. Multistorage device 113k is electrically connected to computer 115 by line 116.

Figure 3:
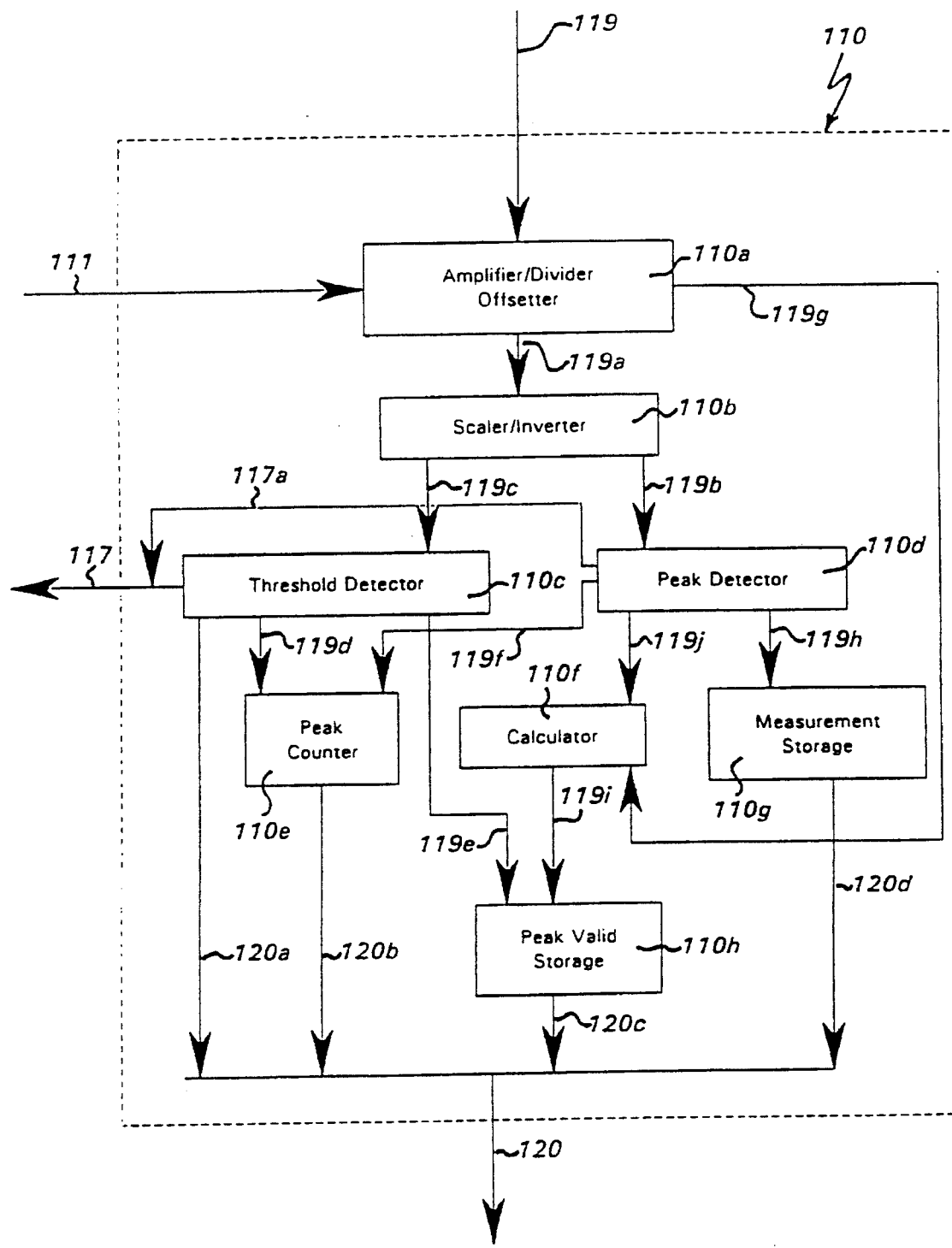
FIG. 3 schematically depicts in detail the processor in the apparatus of FIG. 1.

As depicted schematically in FIG. 3, processor 110 comprises amplifier/divider/offsetter 110a electrically connected to detector 109 by line 111, detector 118 by line 119, calculator 110f by line 119g and scaler/inverter 110b by line 119a. Scaler inverter 110b is electrically connected to threshold detector 110c by line 119c and peak detector 110d by line 119b. Threshold detector 110c is electrically connected to processor/timer 113 by line 117, computer 115 by line 120a and line 120, peak counter 110e by line 119d and peak valid storage 110h by line 119e. Peak detector 110d is electrically connected to processor/timer 113 via lines 117a and 117, peak counter 110e by line 119f, calculator 110f by line 119j and measurement storage 110g by line 119h. Peak counter 110e is electrically connected to computer 115 by lines 120b and 120, calculator 110f is electrically connected to peak valid storage 110h by line 119i, peak valid storage 110h is electrically connected to computer 115 by lines 120c and 120 and measurement storage 110g is electrically connected to computer 115 by tines 120d and 120.

In operation, a method for determining the mean and standard deviation of a plurality of diameters of wool fibres, includes passing a validating and measurement laser beam from laser 101 through pinhole 102 and via splitter 103 to form a pinhole diffraction pattern in the interaction volume in cell 105 and a reference pinhole diffraction pattern in the plane of reference detector 109 which detects the intensity of the reference pinhole diffraction pattern to produce a reference signal. The reference signal from detector 109 is passed to processor 110 via line 111 where it is amplified by amplifier/divider/offsetter 110a to produce an amplified reference signal. The periphery of detector 109 is in about the same position as the first minimum of the reference pinhole diffraction pattern. In the event that there is no wool fibre in the interaction volume, a baseline pinhole diffraction pattern is formed in the plane of detector 118 which is detected by detector 118 to produce two baseline signals, designated baseline signals Ab and Bb. The baseline signals from the top and bottom halves of detector 118 are separately passed to processor 110 by line 119, amplified and divided by the amplified reference signal, obtained at the same time, by amplifier/divider/offsetter 110a, to produce normalised baseline signals Abn and Bbn. The periphery of detector 118 is in about the same position as the first minimum of the baseline pinhole diffraction pattern. The sum of the normalised baseline signals Abn+Bbn is offset to zero by the amount BL by amplifier/divider/offsetter 110a. A wool fibre in the isopropanol-wool slurry is passed through the interaction volume to produce measurement outgoing light which is in the form of a diffraction pattern comprising the optical superposition of the pinhole diffraction pattern and the diffraction pattern produced by the interaction of the wool fibre and the expanding laser beam in the interaction volume, the measurement outgoing light passing through splitter 104 and being detected by detector 118 to produce two measurement signals from the top and bottom halves of split detector 118, designated measurement signals Am and Bm. The measurement signals from detector 118 are separately passed to processor 110 by line 119, amplified and divided by the amplified reference signal, obtained at the same time, to produce normalised measurement signals Amn and Bmn which are made available to calculator 110f via line 119g.

The sum of the normalised measurement signals Amn+ Bmn is offset by BL by amplifier/divider/offsetter 110a and passed to scaler/inverter 110b via line 119a. Scaler/inverter 110b scales and inverts the signal to produce a measurement signal M where the scaling allows M to remain within the dynamic range of processor 110 for the largest diameter fibre to be measured corresponding to a largest allowed measurement signal Mm. The value M is passed to threshold detector 110c via line 119c and peak detector 110d via line 119b.

When threshold detector determines that the measurement signal M exceeds a threshold of typically 1%–10% of Mm, an above threshold signal is passed to processor/timer 113 via line 117, a peak valid signal Vp in peak valid storage 110h is set to "FALSE" via line 119e and peak counter 110e is set to zero via line 119d. As the wool fibre passes through the interaction volume, measurement signal M passes through a maximum due to the occlusion of the expanding laser beam in the interaction volume by the wool fibre which maximum is peak detected by peak detector 110d, typically within 100 microseconds, more typically within 5 microseconds of the peak, upon which peak counter 110e is incremented via line 119f, a peak detect signal is sent to processor/timer 113 via lines 117a and 117, the maximum value Mp of measurement signal M is passed to measurement storage 110g via line 119h, measurement storage 110g stores Mp, the values Amn and Bmn are accepted by calculator 110f from amplifier/divider/offsetter 110a via line 119g as directed by peak detector 110d via line 119j, calculator 110f calculates result |(Amn−Bmn)|, which value may be indicative of whether the wool fibre fully traversed the interaction volume at the time of the peak. If the result is less than typically 10%, more typically 3% of the value of Mp, calculator 110f sets the peak valid signal Vp in peak valid storage 110h to "TRUE" via line 119i. If peak detector 110d detects a second peak in measurement signal M while M remains above threshold, peak counter 110e is incremented a second time via line 119f.

When threshold detector 110c detects that the measurement signal M falls below threshold, it sends a data available signal to computer 115 via lines 120a arid 120 upon which computer 115 reads the peak value of the measurement signal Mp stored in measurement storage 110g via lines 120d and 120, the peak valid signal Vp stored in peak valid storage 110 via lines 120c and 120 and the value stored in peak counter 110e via lines 120b and 120.

Validating outgoing light from the interaction volume is deflected by splitter 104 and focussed by objective 106 to produce an in focus magnified transmission image of the wool fibre in the interaction volume in the plane of end 107 of bundle 108. Light falling on the cores of fibres in bundle 108 at end 107 is guided to the array of 17 photodiode detectors of detector 112. Each of the 17 photodiode detectors detects the intensity of light guided by its corresponding fibre in bundle 108 to produce an output signal which is fed to current to voltage converter 113a via line 114. Converter 113a produces output voltages proportional to each of the light intensity detected by the corresponding photodiodes of detector 112. Each output voltage is passed to amplifier 113b via line 114a. Amplifier 113b amplifies and limits the bandwidth of each output voltage to produce amplified signals which are passed to the inputs of three pole butterworth filters 113c via line 114b and the numerator input of analogue dividers 113d via line 114d. Filter 113c generates low frequency (substantially DC) signals that track the baseline intensities detected by the corresponding photodiodes in detector 112. The output of each butterworth filter in falter 113c is passed to the denominator input of analogue dividers 113d via line 114c. The function of each analogue divider in divider 113d is to normalise each signal detected in detector 112 so that each of these signals can be compared to a common voltage reference in comparator 113e. Thus the normalisation process carried out by circuits 113a, 113b, 113c and 113d allows for variations between fibres in bundle 108. If this was not done fibre bundle 108 would be extremely difficult and costly to manufacture and mount. The normalised output of each analogue divider in divider 113d is fed to comparator 113e via line 113e. Comparator 113e compares the normalised output signal levels from divider 113d via line 114e with a voltage reference to produce a 17 bit binary data word representative of the image focussed onto the fibres at end 107.

The binary word is passed from circuit 113e to a change detection circuit, comprising state machine 113f electrically connected to magnitude comparator 11L3j via line 114i. The function of the change detection circuit is to detect and latch any change from the current binary word passed from comparator 113e via line 114f which occurs whenever there is a significant change in the image focussed by lens 106 on end 107.

Before an above threshold signal is fed to state machine 113f, via line 117, computer 115 enables state machine 113f via lines 116 and 116a and state machine 113f resets a memory storage pointer in multi storage circuit 113k, via line 114k to the beginning of storage circuit 113k. State machine 113f begins the data gathering process when an above threshold signal is received from processor 110 via line 117. At the start of the data gathering process timer 113g is reset by state machine 113f via line 114g and begins counting and a busy flag is set in state machine 113f which busy flag can be monitored by computer 115 via lines 116a and 116. During the data gathering process, state machine 113f stores the first binary word as a binary value in an input register. The contents of this register are compared to the current binary word using magnitude comparator 113j and line 114i. State machine 113f detects an inequality in comparator 113j via line 114i and assembles the change in the data word from comparator 113e, along with the time read from timer 113g via line 114g, sends it to multi storage circuit 113k via line 114k, increments the memory storage pointer in multi storage circuit 113k, via line 114k and stores the new word in the input register which removes the inequality in magnitude comparator 113j. When the peak detect signal is received by state machine 113f from processor 110 via line 117, countdown timer 113h is started via line 114h. The countdown timer typically runs down in 60 micro seconds, which is detected by state machine 113f via line 114h upon which a last data word from comparator 113e via line 114f and corresponding time from timer 113g via line 114g is assembled by state machine 113f and sent to multistorage 113k via line 114k, the data gathering process is stopped and the busy flag is cleared.

Computer 115 monitors the data busy flag from state machine 113f via lines 116 and 116a to determine whether data is available for reading and processing. If computer 115 receives the data available signal from threshold detector 110c via lines 120a and 120, it reads the maximum value of the measurement signal Mp from measurement storage 110g via lines 120d and 120, the peak valid signal Vp from peak valid storage 110h via lines 120c and 120 and the value stored in peak counter 110e via lines 120b and 120. Computer 115 then reads the data words and times stored in multi storage 113k via line 116 in reverse order, monitoring the times, until the time monitored is less than a calculated value. The calculated value is a predetermined amount, typically 120 microseconds, less than the first time stamp read in by computer 115. For example, if the data gathering process was stopped at a time stamp of 160 microseconds, computer 115 would typically stop reading data when the time stamp monitored was less than 40 microseconds.

After reading in the data, computer 115 determines from the value of the peak valid signal Vp and the number of counts stored in the peak counter whether one wool fibre may have completely spanned the interaction volume to give rise to the maximum value of the measurement signal Mp. If so computer 115 confirms, from the data words read in, whether one wool fibre completely spanned the interaction volume about the time Mp was determined and stored. If the confirmation is true, computer 115 calculates the diameter of the wool fibre from Mp using a calibration look up table and stores it in its memory.

Apparatus 100 repeats the above procedure and thereby determines from resultant stored wool fibre diameters the mean and standard deviation.

Figure 6A:
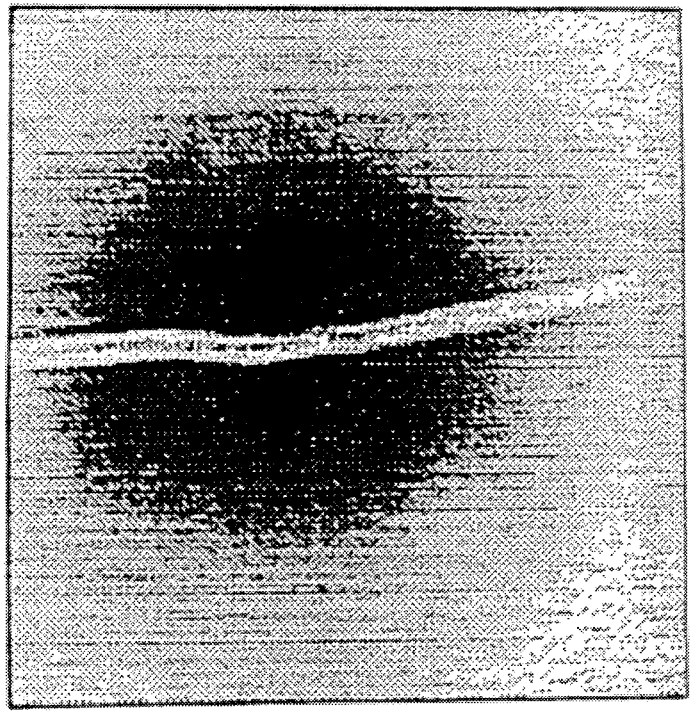
FIG. 6(a) is a typical reverse image of a 15 micrometer diameter wool fibre in the plane of end 107 of apparatus 100 of FIG. 1.
Figure 6B:
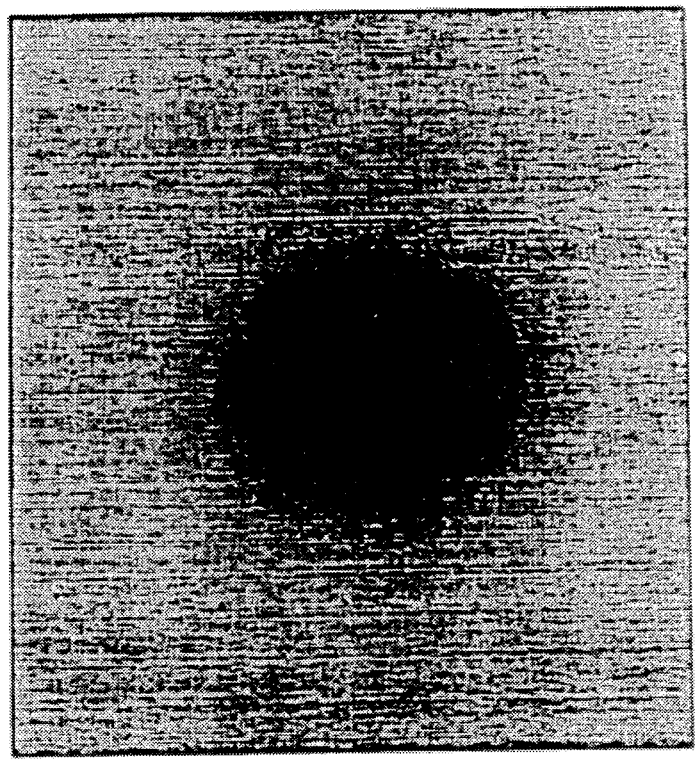
FIG. 6(b) is a typical reverse image of a 15 micrometer diameter wool fibre in the plane of detector 118 of apparatus 100 of FIG. 1.
Figure 7A:
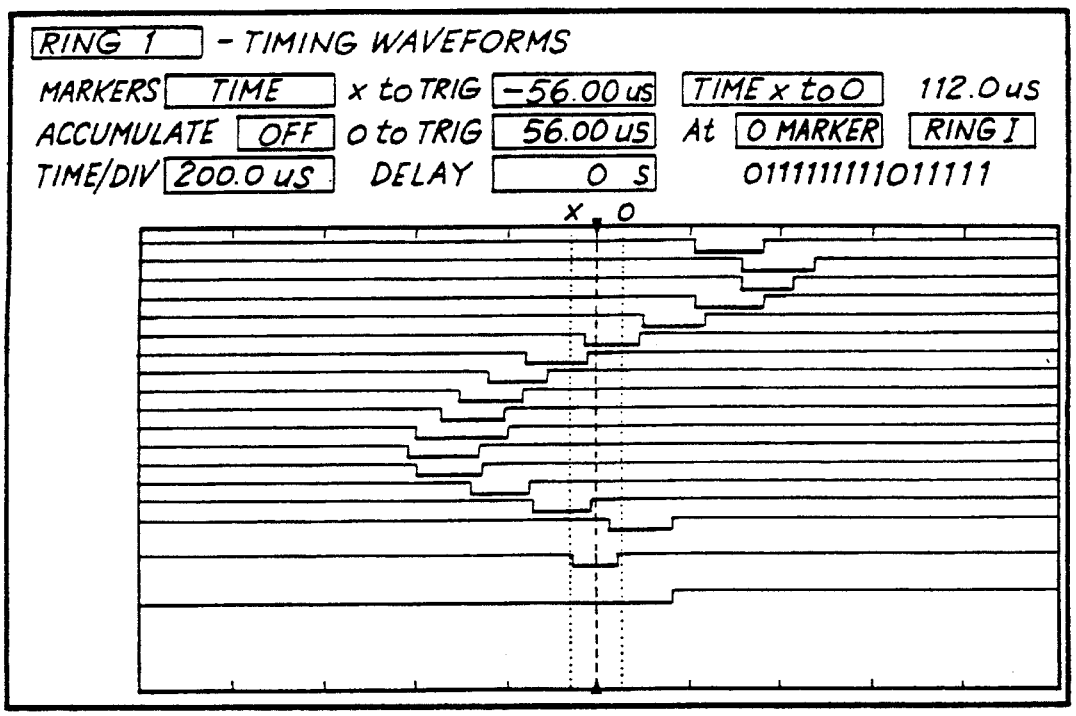
FIGS. 7(a)–(d) show typical signals passed by comparator 113e to state machine 113f via line 114f of processor/timer 113 of FIG. 5 of apparatus 100 of FIG. 1.
Figure 7B:
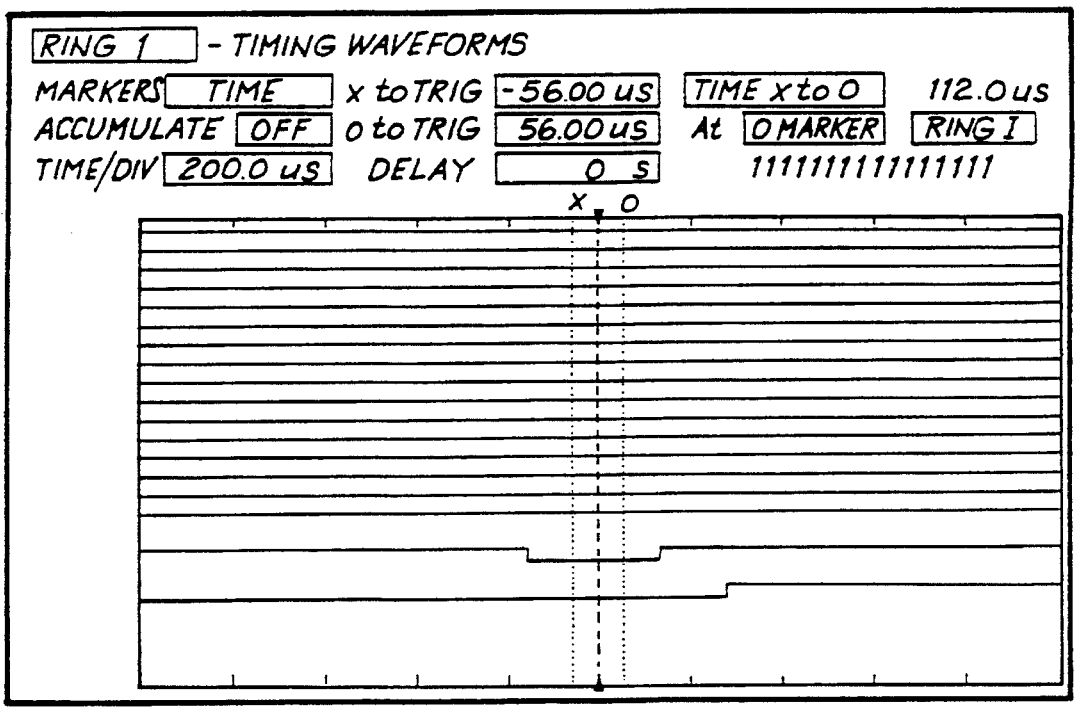
Figure 7C:
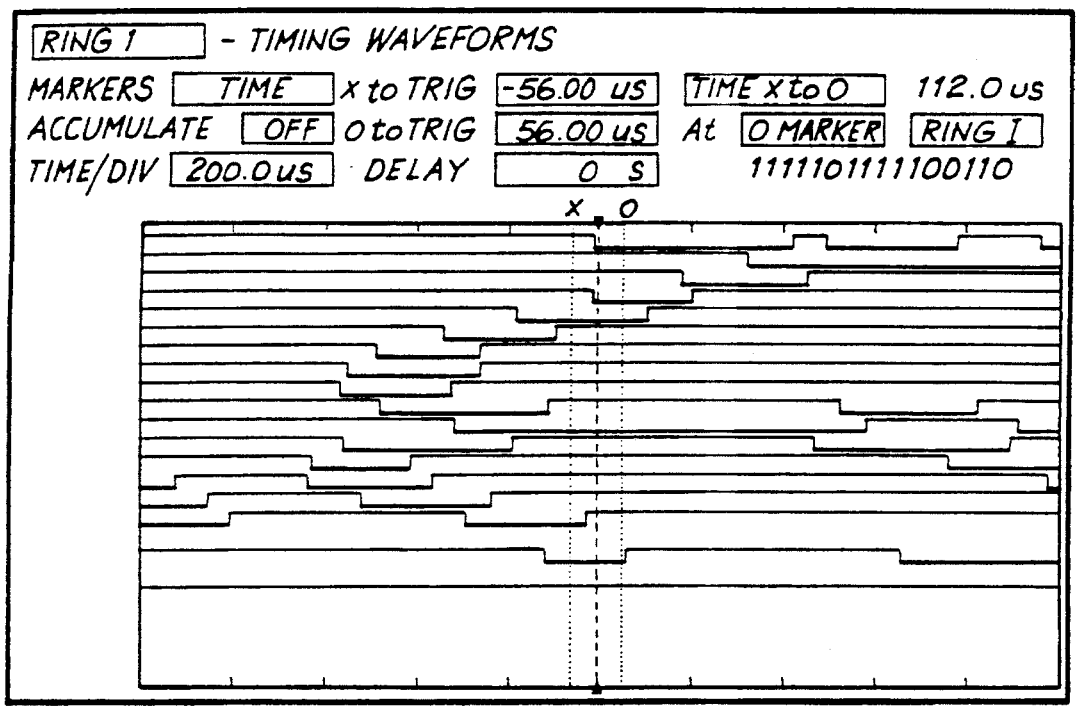
Figure 7D:
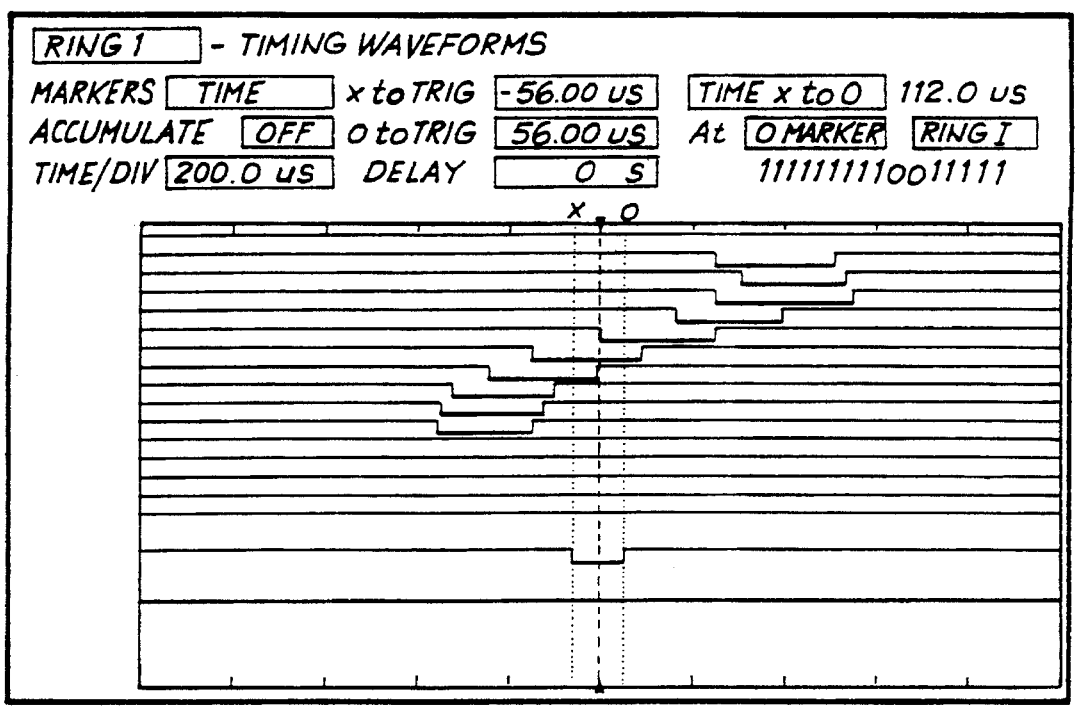

A typical reverse image of a 15 micrometer diameter wool fibre in the plane of end 107 is depicted in FIG. 6(a). A typical reverse image of a 15 micrometer diameter wool fibre in the plane of detector 118 is depicted in FIG. 6(b). Note that the image of FIG. 6(a) shows features position, orientation, modulation and colour of the wool fibre whereas the image of FIG. 6(b) does not distinguish such features. FIGS. 7(a)–(d) show typical signals passed by comparator 113e to state machine 113f via line 114f. FIG. 7(a) results from a valid wool fibre, that is, a wool fibre in a valid position and orientation that completely crosses the interaction volume such as the wool fibre depicted in FIG. 6(a). FIG. 7(b) results from an invalid object, namely a wool fragment that does not completely cross the interaction volume, passing through the interaction volume. FIG. 7(c) results from an invalid object, namely two wool fibres that pass through the interaction volume simultaneously. FIG. 7(d) results from an invalid object, namely a wool fibre that does not completely cross the interaction volume, passing through the interaction volume.

Figure 2:
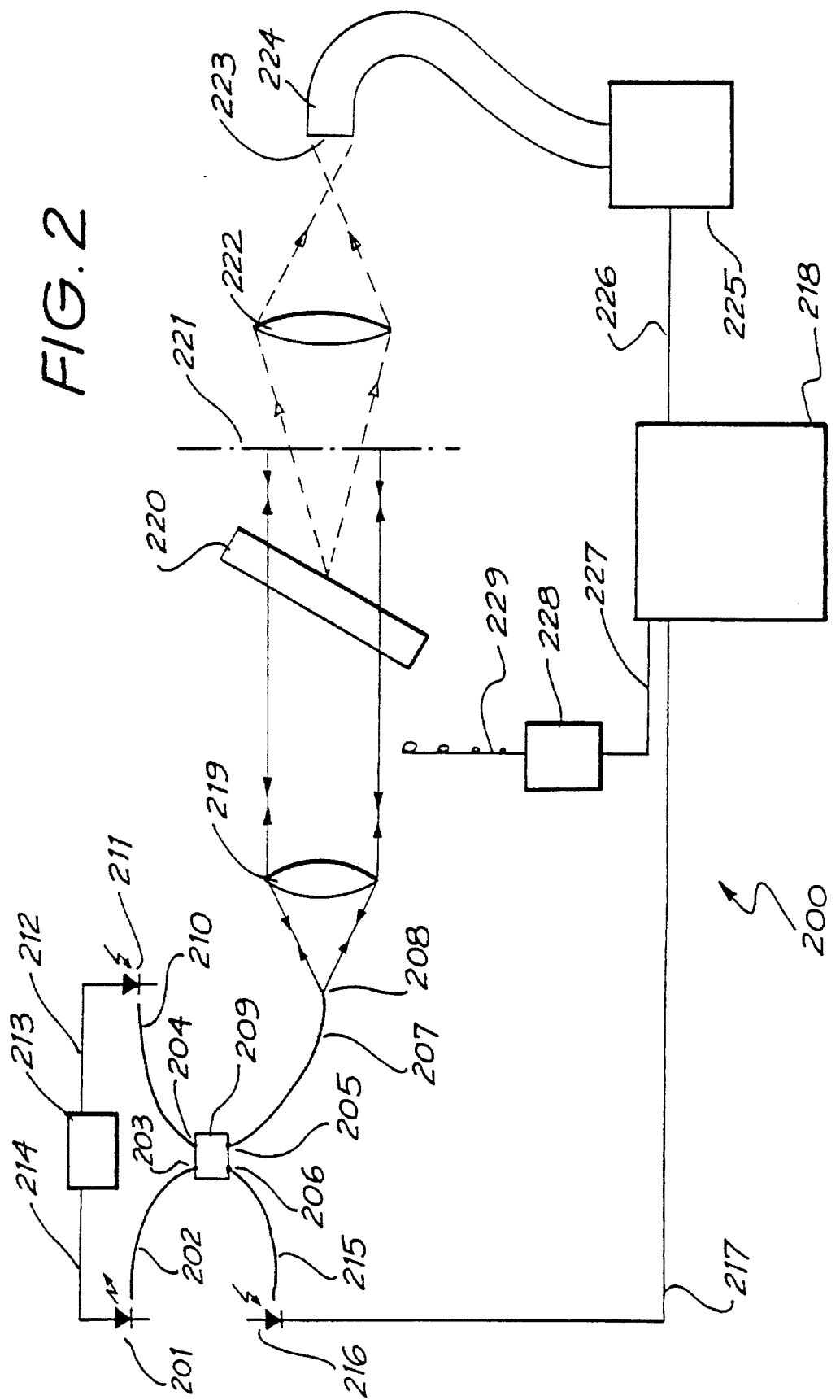
FIG. 2 schematically depicts an alternative apparatus for determining a the mean and standard deviation of a plurality of diameters of wool fibres, in accordance with the invention.

Referring to FIG. 2 an apparatus 200 for determining the mean and standard deviation of a plurality of diameters of wool fibres, includes a validating and measurement optically isolated laser diode 201 which injects validating and measurement laser light into the core of single mode fibre 202. Fibre 202 is optically connected to single mode coupler 209 having ports 203, 204, 205 and 206. Port 205 of coupler 209 is optically connected to single mode fibre 207 having exit end 208. Port 204 of coupler 209 is optically connected to photodiode 211 by fibre 210. Photodiode 211 is electrically connected to laser diode power supply 213 by line 212. Supply 213 is electrically connected to laser 201 by line 214. Port 206 of coupler 209 is optically connected to measurement photo diode 216 by fibre 215. Diode 216 is electrically connected to computer 218 by line 217. Collimating lens 219 collimates validating and measurement laser light emerging from the core of fibre 207 at end 208 to form a collimated validating and measurement laser beam typically about 350 micrometers in diameter having an approximately gaussian intensity profile. The collimated laser beam passes through a validating and measurement interaction volume defined by the intersection of the beam and tapered cell 220 which is oriented not normal to the direction of travel of the collimated beam. A detailed description of cell 220 is contained in Australian Patent no. 599 053. When apparatus 200 is operating wool fibres in an isopropanol slurry pass through cell 220 generally at a non-zero degree angle to the direction of slurry flow through cell 220 to scatter, reflect, diffract, absorb, refract and otherwise interact with the collimated beam. Partial mirror 221 reflects measurement outgoing light from the interaction volume, a portion of which is reinjected into end 208 of fibre 207 to be detected by diode 216. Partial mirror 221 transmits validating outgoing light from the interaction volume. Lens 222 is operatively disposed with respect to end 208, lens 219 and cell 220 to produce, using validating outgoing light transmitted by partial mirror 221, a highly visible diffraction pattern from wool fibres in the interaction volume in the plane of end 223 of 12 400 micrometer glass cored 12.5 micrometer thick plastic clad fibre bundle 224 comprising at end 223 a close packed circularly symmetric core configuration. Bundle 224 is optically connected to validating detector and neural network 225 which is electrically connected to computer 218 by line 226. Sample carrier 229 is mechanically attached to mechanical stage 228 which is electrically connected to computer 218 by line 227.

In operation, a method for determining the mean and standard deviation of a plurality of diameters of wool fibres, includes guiding validating and measurement laser light from diode 201 to end 208, via fibre 202, ports 203 and 205 of coupler 209 and fibre 207, from which it emerges with a numerical aperture of typically 0.1. Lens 219 collimates the validating and measurement light emerging from end 208 to form a collimated validating and measurement beam which passes through cell 220. In the event that there is no wool fibre in the interaction volume, the collimated beam passes through cell 220 and is partially reflected as uninteracted measurement light by partial mirror 221 back through cell 220. The uninteracted measurement light, still collimated, is focussed by lens 219 and injected into the core of fibre 207 at end 208 and enters coupler 209 via fibre 207 and port 205. A portion of the uninteracted measurement light entering coupler 209 leaves coupler 209 by port 206 to be guided by fibre 215 to diode 216 where it is detected to produce a baseline signal Mb which is fed to computer 218 via line 217. A wool fibre in the isopropanol-wool slurry is passed through the interaction volume to partially occlude the collimated validating and measurement beam, thereby producing a validating and measurement outgoing light beam. A portion of the outgoing light is reflected by partial mirror 221 back through cell 220 where it again interacts with the wool fibre to form the measurement outgoing light beam. A portion of the measurement outgoing light beam is injected into the core of fibre 207 at end 208 a portion of which is guided to diode 216 via fibre 207, ports 205 and 206 of coupler 209 and fibre 215 where it is detected to produce a measurement signal Mm which is fed to computer 218 via line 217. Because of the geometry of the core at end 208 of fibre 207, lens 219 and partial mirror 221, validating and measurement light source 201 is effectively at infinity and measurement photodiode 216 is effectively at infinity. Therefore, measurement signal Mm is substantially independent of wool fibre diameter independent parameters, such as axial position along the collimated validating and measurement beam, fibre medcuation and fibre colour, and when a single wool fibre completely crosses the collimated validating and measurement beam in the interaction volume and is centred in the collimated validating and measurement beam, the signal Mm will depend almost solely on the diameter of the fibre. (Note that there are some minor orientation effects due to the polarisation of the collimated validating and measurement beam.) When Mm passes through a minimum, computer 218 interrupts its current task, stores the minimum Mmm, the minimum time at which the minimum occurred and the last baseline signal Mb in temporary memory.

The optical power of the laser light injected into the core of fibre 202 by laser 201 is maintained at a constant level by feedback control as follows. A predetermined amount of the light injected into the core of fibre 202 by laser 201 is guided to photodiode 211, via fibre 202, ports 203 and 204 of coupler 209 and fibre 210, which detects the light level and produces a light level signal which is proportional to the light level detected by diode 211. The light level signal is passed to supply 213 via line 212. Supply 213 adjusts the current fed to diode 201 via line 214 to keep the light level signal constant at some predetermined value.

The portion of the validating and measurement outgoing light beam that passes through partial minor 221 as validating outgoing light is focussed by lens 222 to form a highly visible diffraction pattern at end 223 of bundle 224. A portion of the highly visible diffraction pattern enters the cores of the fibres in bundle 224 at end 223 to be guided to and detected by validating detector and neural network 225. Validating detector and neural network 225 has previously been 'taught' to recognise the time at which a single wool fibre completely crosses the collimated validating and measurement beam in the interaction volume and is centred in the collimated validating and measurement beam. When validating detector and neural network 225 encounters such a signal, it passes a true validation signal to computer 218 via line 226 together with the validation true time at which the validation detector and neural network received the corresponding validation outgoing light via bundle 224. Computer 218 then interrupts its current task and stores the validation true time and increments a valid fibre counter.

When it is not busy storing measurement and validation signals, computer 218 matches each validation true time with the corresponding minimum time, calculates the occlusion percentage Oc from the corresponding minimum Mmm and baseline signal Mb using the formula Oc=100 (1−Mmm/Mb). The fibre diameter is then determined from the occlusion percentage using a calibration curve, the obtaining of which will be described below, and stores the fibre diameter in permanent memory. Minimum, baseline signals and minimum times that don't correspond closely with validation true times are discarded. Validation true times that don't correspond closely with minimum times are discarded and for each validation true time discard, the valid fibre counter is decremented.

The above process is repeated until the valid fibre counter reaches a predetermined amount, typically 1,000 to 10,000, at which time computer 218 matches the remaining minimum times and validation true times and determines and stores the corresponding fibre diameters in permanent memory. Once all of the fibre diameters have been stored in permanent memory, computer 218 determines from the permanently stored wool fibre diameters the mean and standard deviation.

The calibration curve is obtained as follows. A calibration sample with a range of typically wire fibres having known diameters typically in the range of 5 micrometers to 200 micrometers is placed on sample carrier 229. Computer 218 then directs mechanical stage 228, via line 227, to pass the calibration sample through the collimated validating and measurement beam. The minimum Mmm resulting from the passage of each fibre in the calibration sample through the collimated validating and measurement beam, together with the baseline signal Mb accepted by computer 218 between each accepted Mmm signal, is stored by computer 218 and each minimum Mmm is matched with the corresponding known diameter. This process is repeated a number of times, typically in excess of 10 times, and the average occlusion percentage Oc determined for each calibration fibre. A calibration curve is then fitted to the occlusion percentages and known diameters and the calibration curve is stored by computer 218.

In an alternative mode of operation apparatus 200 determines the mean and standard deviation as follows. A sample comprising wool fibres of unknown diameter are placed on sample carrier 229 and passed through the collimated validating and measurement beam and the mean and standard deviation of the diameters of the fibres in the sample determined as described above. In this instance, the validating and measurement interaction volume is defined by the intersection of the sample on the sample carrier and the collimated validating and measurement beam when the sample is passed through the beam. Since the highly visible diffraction pattern produced by the wool fibres and lens 222 on end 223 of bundle 224 will be different to that described above, the algorithm used by validating detector and neural network 225 will also be different.

INDUSTRIAL APPLICABILITY

The methods and apparatus of the invention may be utilised to determine a first parameter(s) of a valid object, such as shape, diameter, area, chemical composition, colour, number of parts, thickness, width, length, absorptivity, reflectivity, transmittivity, dielectric constant, Raman scattering profile, fluorescence, surface texture or other surface detail, position, orientation, surface tension, surface roughness, surface profile or density, for example. In the case of a fibrous object for example the first parameter may be diameter, for example. The measurements may be readily performed on a plurality of objects and statistical information readily determined from the measurements.

We claim:

1. A method for determining a measurement parameter of a fibrous object and whether the object is a valid object, comprising:

(a) passing a validating energy beam through a validating interaction volume;

(b) detecting validating outgoing energy originating from the validating energy beam in the validating interaction volume, the detection being in at least one validating focal plane of the validating outgoing energy with respect to the validating interaction volume and determining a validating parameter from the detected validating outgoing energy wherein the validating parameter is indicative of whether an object in the validating interaction volume is a single object in a valid measuring position and orientation;

(c) determining from the validating parameter whether the validating outgoing energy originated from an interaction between a fibrous object and validating beam in the validating volume and, on determining an object;

(d) passing a measurement energy beam through the measurement interaction volume, said measurement interaction volume being the same as the validating interaction volume, to interact with the object whereby at least a part of the measurement energy beam is occluded by the fibrous object so as to produce measurement outgoing energy in the form of a diffraction pattern;

(e) detecting a portion of the measurement outgoing energy in at least one measurement focal plane of the measurement outgoing energy with respect to the measurement interaction volume, the measurement focal plane being different from the validating focal plane, and wherein the detected portion of said measurement outgoing energy is not so much that parameters independent of the measurement parameter prevent determination of the measurement parameter from the measurement outgoing energy to a required accuracy and determining a measurement parameter to the required accuracy from the detected measurement outgoing energy; and (f) determining from the validating parameter whether the fibrous object is a valid object, said object being a valid object when it is a single object in a valid measuring position and orientation; and, on determining a valid object, determining a first parameter of the valid fibrous object from the measurement parameter and determining the first parameter of the valid fibrous object as an acceptable valid object parameter wherein the first parameter is a diameter of the fibrous object.

2. A method for determining a measurement parameter of a valid object, comprising:

the method of claim 1; and, on determining a valid object, determining the measurement parameter of the valid object as an acceptable valid object parameter.

3. A method for determining a measurement parameter of an invalid object, comprising:

the method of claim 1; and, on determining an invalid object, determining the measurement parameter of the invalid object as an unacceptable valid object parameter.

4. The method of claim 1 wherein the validating energy beam is the same as the measurement energy beam and is a collimated light beam;

the validation interaction volume is the same as the measurement interaction volume and is one interaction volume;

the validating parameter is the intensity from at least part of an image of the interaction volume produced using the validating outgoing energy, the validating outgoing energy being in the form of light; and the measurement parameter is the intensity of at least a portion of the measurement outgoing energy said measurement outgoing energy being a diffraction pattern.

5. The method of claim 1 wherein a valid fibrous object comprises a fibre selected from a group including fibreglass fibre, hessian fibre, nylon fibre, glass fibre, polnosic fibre, polyester fibre, abaca fibre, silk fibre, jute fibre, flax fibre, cellulose fibre, regenerated fibre, sisal fibre, carbon fibre, stainless steel fibre, vegetable fibre, polyolefin fibre, steel fibre, boron fibre, copper fibre, brass fibre, teflon fibre, dacron fibre, mylar fibre, aluminium fibre, aluminium alloy fibre, polyamide fibre, polyacrylic fibre, nylon 66 polyacrylonitrile fibre, polyvinyl alcohol fibre, edible vegetable fibre, inedible vegetable fibre, wood pulp fibre, cotton fibre, animal fibre, meat fibre, sheep wool fibre, hair, human hair, goat hair, cattle hair, yarn, wool yarn, cotton yarn, string, wire and optical fibre; and has a preselected length in a preselected position and orientation in the validation and measurement interaction volume.

6. The method of claim 1 wherein the validating energy beam is the same as the measurement energy beam and is an expanding beam of light emerging from a pinhole illuminated by a collimated light beam;

the validation interaction volume is the same as the measurement interaction volume and is one interaction volume;

the validating parameter is the intensity from at least part of an image of the interaction volume produced using the validating outgoing energy, the validating outgoing energy being in the form of light;

the measurement parameter is the intensity of at least a portion of the measurement outgoing energy said measurement outgoing energy being a diffraction pattern;

a valid object comprises a fibre selected from the group consisting of a sheep wool fibre and goat hair; and has a preselected length in a preselected position and orientation in the validation and measurement interaction volume and the first parameter is the diameter of the fibre; and the method further comprises repeating the method of claim 1 a plurality of times and determining statistical information in respect of a plurality of the diameters of this valid object.

7. The method of claim 1 wherein the validating energy beam is the same as the measurement energy beam and is a collimated light beam;

the validation interaction volume is the same as the measurement interaction and is one interaction volume;

the validating parameter is the intensity from at least part of an image of the interaction volume produced using the validating outgoing energy, the validating outgoing energy being in the form of light;

the measurement parameter is the intensity of at least a portion of the measurement outgoing energy said measurement outgoing energy being a diffraction pattern;

a valid object comprises a fibre selected from the group consisting of a sheep wool fibre and goat hair; and has a preselected length in a preselected position and orientation in the validation and measurement interaction volume and the first parameter is the diameter of the fibre; and the method further comprises repeating the method of claim 1 a plurality of times and determining statistical information in respect of a plurality of the diameters of the valid object.

8. A method for determining a diameter of a fibrous object and determining a first parameter of an invalid object, comprising:

passing a validating energy beam through a validating interaction volume;

detecting validating outgoing energy originating from the validating energy beam in the validating interaction volume, the detection being in at least one validating focal plane of the validating outgoing energy with respect to the validating interaction volume and determining a validating parameter from the detected validating outgoing energy;

determining from the validating parameter whether the validating outgoing energy originated from an interaction between said fibrous object and the validating beam in the validating volume and, on determining said fibrous object;

locating said fibrous object in a measurement interaction volume;

passing a measurement energy beam through the measurement interaction volume to interact with said fibrous object so as to produce measurement outgoing energy;

detecting at least a portion of the measurement outgoing energy in at least one measurement focal plane of the measurement outgoing energy with respect to the measurement interaction volume, the measurement focal plane being different from the validating focal plane, and determining a measurement parameter from the detected measurement outgoing energy; and determining from the validating parameter whether the fibrous object is a valid object;

determining the diameter of the fibrous object from the measurement parameter; and, on determining an invalid object, determining the first parameter of the invalid object as an unacceptable valid object parameter.

9. A method for determining a measurement parameter of a valid object and determining a measurement parameter of an invalid object, comprising:

passing a validating energy beam through a validating interaction volume;

detecting validating outgoing energy originating from the validating energy beam in the validating interaction volume, the detection being in at least one validating focal plane of the validating outgoing energy with respect to the validating interaction volume and determining a validating parameter from the detected validating outgoing energy;

determining from the validating parameter whether the validating outgoing energy originated from an interaction between a fibrous object and the validating beam in the validating volume and, on determining an object;

locating the fibrous object in a measurement interaction volume;

passing a measurement energy beam through the measurement interaction volume to interact with the fibrous object so as to produce measurement outgoing energy;

detecting at least a portion of the measurement outgoing energy in at least one measurement focal plane of the measurement outgoing energy with respect to the measurement interaction volume, the measurement focal plane being different from the validating focal plane, and determining a measurement parameter from the detected measurement outgoing energy; and determining from the validating parameter whether the fibrous object is a valid object; and, (I) on determining a valid object, determining the measurement parameter of the valid object as an acceptable valid object parameter, wherein said measurement parameter is a diameter of the fibrous object;

(II) on determining an invalid object, determining the measurement parameter of the invalid object as an unacceptable valid object parameter.

10. A method for determining a diameter of a fibrous object and determining a measurement parameter of an invalid object, comprising:

passing a validating energy beam through a validating interaction volume;

detecting validating outgoing energy originating from the validating energy beam in the validating interaction volume, the detection being in at least one validating focal plane of the validating outgoing energy with respect to the validating interaction volume and determining a validating parameter from the detected validating outgoing energy;

determining from the validating parameter whether the validating outgoing energy originated from an interaction between the fibrous object and the validating beam in the validating volume and, on determining the fibrous object;

locating the fibrous object in a measurement interaction volume;

passing a measurement energy beam through the measurement interaction volume to interact with the fibrous object so as to produce measurement outgoing energy;

detecting at least a portion of the measurement outgoing energy in at least one measurement focal plane of the measurement outgoing energy with respect to the measurement interaction volume, the measurement focal plane being different from the validating focal plane, and determining a measurement parameter from the detected measurement outgoing energy; and determining from the validating parameter whether the fibrous object is a valid object; and, (I) on determining a valid object, determining the diameter of the fibrous object from the measurement parameter;

determining the diameter of the valid object as an acceptable valid object parameter;

(II) on determining an invalid object, determining the measurement parameter of the invalid object as an unacceptable valid object parameter.

11. The method of any one of claims 1 or 3 to 7 wherein the validating energy beam is the same as the measurement energy beam and is an expanding beam of light emerging from a pinhole illuminated by a collimated light beam;

the validation interaction volume is the same as the measurement interaction volume and is one interaction volume;

the validating parameter is the intensity from at least part of an image of the interaction volume produced using the validating outgoing energy, the validating outgoing energy being in the form of light; and the measurement parameter is the intensity of at least a portion of the measurement outgoing energy said measurement outgoing energy being a diffraction pattern.

12. An apparatus for determining a measurement parameter of a fibrous object and whether the object is a valid object, comprising:

(a) a validating energy source for passing a validating energy beam through a validating interaction volume;

(b) a validating detector for detecting validating outgoing energy originating from the validating energy beam in the validating interaction volume, the detection being in at least one validating focal plane of the validating outgoing energy with respect to the validating interaction volume and means for determining a validating parameter from the detected validating outgoing energy operatively associated with the validating detector, the validating parameter being a diameter of the fibrous object, the validating detector being operatively associated with the validating energy source wherein the validating parameter is indicative of whether the fibrous object in the validating interaction volume is a single object in a valid measuring position and orientation;

(c) verification means for determining from the validating parameter whether the validating outgoing energy originated from an interaction between the fibrous object and the validating beam in the validating volume, the verification means being operatively associated with the validating detector;

(d) a measurement energy source for passing a measurement energy beam through a measurement interaction volume, said measurement interaction volume being the same as the validating interaction volume, to interact with the fibrous object whereby at least a part of the measurement energy beam is occluded by the fibrous object so as to produce measurement outgoing energy in the form of a diffraction pattern;

(e) a measurement detector for detecting a portion of the measurement outgoing energy in at least one measurement focal plane of the measurement outgoing energy with respect to the measurement interaction volume, the measurement focal plane being different from the validating focal plane, and wherein the detected portion of said measurement outgoing energy is not so much that parameters independent of the measurement parameter prevent determination of the measurement parameter from the measurement outgoing energy to a required accuracy and means for determining a measurement parameter from the detected measurement outgoing energy operatively associated with the measurement detector, the measurement detector being operatively associated with the measurement energy source; and (f) means for determining from the validating parameter whether the fibrous object is a valid object, the means for determining being operatively associated with the validating detector, the fibrous object being a valid object when it is a single object in a valid measuring position and orientation.

13. An apparatus as in claim 12 which includes:

means for determining the first parameter of the object from the measurement parameter, operatively associated with the measurement detector.

14. An apparatus as in claim 12 which includes:

means for determining the first parameter of the valid object from the measurement parameter and for determining the first parameter of the valid object as an acceptable valid object parameter, operatively associated with the measurement detector and the means for determining from the validating parameter whether the object is a valid object.

15. An apparatus as in claim 12 which includes:

means for determining the measurement parameter of the valid object as an acceptable valid object parameter, operatively associated with the measurement detector and the means for determining from the validating parameter whether the object is a valid object.

16. An apparatus as in claim 12 which includes:

means for determining the measurement parameter of the invalid object as an unacceptable valid object parameter, operatively associated with the measurement detector and the means for determining from the validating parameter whether the object is a valid object.

17. An apparatus as in claim 12 which includes:

means for determining the first parameter of the object from the measurement parameter and for determining the first parameter of the invalid object as an unacceptable valid object parameter, operatively associated with the measurement detector and the means for determining from the validating parameter whether the object is a valid object.

18. An apparatus as in claim 12 which includes:

means for determining the measurement parameter of the valid object as an acceptable valid object parameter and for determining the measurement parameter of the invalid object as an unacceptable valid object parameter, operatively associated with the measurement detector and the means for determining from the validating parameter whether the object is a valid object.

19. An apparatus as in claim 12 which includes:

means for determining the first parameter of the object from the measurement parameter and for determining the first parameter of the valid object as an acceptable valid object parameter and for determining the measurement parameter of the invalid object as an unacceptable valid object parameter, operatively associated with the measurement detector and the means for determining from the validating parameter whether the object is a valid object.

20. The apparatus of claim 12 wherein the validating energy source is the same as the measurement energy source;

the validating energy beam is the same as the measurement energy beam and is an expanding beam of light emerging from a pinhole illuminated by a collimated light beam;

the validation interaction volume is the same as the measurement interaction volume and is one interaction volume; and the validating parameter is the intensity from at least part of an image of the interaction volume produced using the validating outgoing energy, the validating outgoing energy being the form of light; and the measurement parameter is the intensity of at least a portion of the measurement outgoing energy said measurement outgoing energy being a diffraction pattern.

21. The apparatus of claim 12 wherein the validating energy source is the same as the measurement energy source;

the validating energy beam is the same as the measurement energy beam and is a collimated light beam;

the validation interaction volume is the same as the measurement interaction volume and is one interaction volume;

the validating parameter is the intensity from at least part of an image of the interaction volume produced using the validating outgoing energy, the validating outgoing energy being in the form of light; and the measurement parameter is the intensity of at least a portion of the measurement outgoing energy said measurement outgoing energy being a diffraction pattern.

22. The apparatus of claim 12 wherein a valid object comprises a fibre selected from a group including fibreglass fibre, hessian fibre, nylon fibre, glass fibre, polnosic fibre, polyester fibre, abaca fibre, silk fibre, jute fibre, flax fibre, cellulose fibre, regenerated fibre, sisal fibre, carbon fibre, stainless steel fibre, vegetable fibre, polyolefin fibre, steel fibre, boron fibre, copper fibre, brass fibre, teflon fibre, dacron fibre, mylar fibre, aluminum fibre, aluminium alloy fibre, polyamide fibre, polyacrylic fibre, nylon 66 polyacrylonitrile fibre, polyvinyl alcohol fibre, edible vegetable fibre, inedible vegetable fibre, wood pulp fibre, cotton fibre, animal fibre, meat fibre, sheep wool fibre, hair, human hair, goat hair, cattle hair, yarn, wool yarn, cotton yarn, string, wire and optical fibre; and has a preselected length in a preselected position and orientation in the validation and measurement interaction volume.

23. The apparatus of claim 12 wherein the validating energy source is the same as the measurement energy source;

the validating energy beam is the same as the measurement energy beam and is an expanding beam of light emerging from a pinhole illuminated by a collimated light beam;

the validation interaction volume is the same as the measurement interaction volume and is one interaction volume;

the validating parameter is the intensity from at least part of an image of the interaction volume produced using the validating outgoing energy, the validating outgoing energy being in the form of light;

the measurement parameter is the intensity of at least a portion of the measurement outgoing energy said measurement outgoing energy being a diffraction pattern;

a valid object comprises a fibre selected from a group including sheep wool fibre and goat hair; and has a preselected length in a preselected position and orientation in the validation and measurement interaction volume and the first parameter is the diameter of the fibre; and the apparatus further comprises means for determining statistical information in respect of a plurality of the diameters of the valid object.

24. The apparatus of claim 12 wherein the validating energy source is the same as the measurement energy source;

the validating energy beam is the same as the measurement energy beam and is a collimated light beam;

the validation interaction volume is the same as the measurement interaction volume and is one interaction volume;

the validating parameter is the intensity from at least part of an image of the interaction volume produced using the validating outgoing energy, the validating outgoing energy being in the form of light;

the measurement parameter is the intensity of at least a portion of the measurement outgoing energy said measurement outgoing energy being a diffraction pattern;

a valid object comprises a fibre selected from the group consisting of a sheep wool fibre and goat hair; and has a preselected length in a preselected position and orientation in the validation and measurement interaction volume and the first parameter is the diameter of the fibre; and the apparatus further comprises means for determining statistical information in respect of a plurality of the diameters of the valid object.

25. The apparatus of claim 12 wherein the validating outgoing energy is light; and further comprising a light focuser to form an image of the validating interaction volume on the validating detector, operatively associated with the validating source and validating detector.

26. The apparatus of claim 12 wherein the measurement outgoing energy is light; and further comprising a light focuser to form an image of the measurement interaction volume on the measurement detector, operatively associated with the measurement source and measurement detector.

27. The apparatus of claim 12 further comprising means to pass an object through the measurement and validating interaction volumes, operatively associated with the validating energy source, measurement energy source and the means for locating.

28. The apparatus of any one of claims 13, 14, 17 and 19 further comprising means for storing and retrieving the measurement parameter(s) and the object validation and for storing the first parameter(s), operatively associated with the measurement detector(s) and the means for determining the first parameter(s) and the means for determining from the validating parameter(s) whether the object is a valid object.

29. The apparatus of any one of claims 12 to 19 wherein the validating detector comprises an array of detecting elements.

30. The apparatus of any one of claims 12 to 19 wherein the measurement detector comprises an array of detecting elements.

31. The apparatus of any one of claims 12 to 19 wherein the validating outgoing energy is light; and the validating detector comprises an optical fibre coupled to a detecting element.

32. The apparatus of any one of claims 12 to 19 wherein the measurement outgoing energy is light; and the measurement detector comprises an optical fibre coupled to a detecting element.

33. An apparatus for determining at least one characteristic of a fibrous object comprising:

a source for generating a beam of radiant energy;

an object receiving sample volume wherein at least a portion of said beam is incident thereon and a portion of which passes therethrough and exits therefrom;

a validating detector positioned at a first focal plane with respect to a beam portion exiting said volume and responsive to radiant energy incident thereon;

circuitry coupled to said detector, for determining a validating parameter, said validating parameter being a diameter of the fibrous object;

verification circuitry, coupled to said determining circuitry, responsive to said validating parameter for determining a source characteristic of said incident radiation;

a measurement detector, positioned at a second focal plane with respect to a beam portion exiting said volume and responsive to radiant energy incident thereon;

circuitry coupled to said measurement detector for determining a measurement parameter;

processing circuitry, coupled to said measurement parameter determining circuitry and to said validating parameter determining circuitry, for determining if the object exhibits the characteristic.

* * * * *